(12) United States Patent
Statham et al.

(10) Patent No.: US 10,064,968 B2
(45) Date of Patent: Sep. 4, 2018

(54) SYSTEMS AND METHODS FOR EMITTING RADIANT ENERGY

(71) Applicant: Skytron, LLC, Grand Rapids, MI (US)

(72) Inventors: Mark Statham, Risingsun, OH (US); Eric Engler, Cass City, MI (US); Steve Fister, Tucson, AZ (US); Robert L. Gilling, Caro, MI (US); Thomas A. Kenny, Troy, MI (US); Rory Sayers, Davison, MI (US); Clinton Starrs, Fenton, MI (US)

(73) Assignee: Skytron, LLC, Grand Rapids, MI (US)

( * ) Notice: Subject to any disclaimer, the term of this patent is extended or adjusted under 35 U.S.C. 154(b) by 0 days.

(21) Appl. No.: 14/464,937

(22) Filed: Aug. 21, 2014

(65) Prior Publication Data
US 2014/0374612 A1    Dec. 25, 2014

Related U.S. Application Data

(63) Continuation of application No. 13/887,684, filed on May 6, 2013, now Pat. No. 8,841,634, which is a
(Continued)

(51) Int. Cl.
*A61L 2/24*     (2006.01)
*G01J 1/32*     (2006.01)
(Continued)

(52) U.S. Cl.
CPC ............. *A61L 2/24* (2013.01); *A61L 2/0047* (2013.01); *A61L 9/20* (2013.01); *G01J 1/32* (2013.01);
(Continued)

(58) Field of Classification Search
CPC . A61L 2/24; A61L 2/0047; A61L 9/20; A61B 6/1542; G01T 1/17
(Continued)

(56) References Cited

U.S. PATENT DOCUMENTS 3,418,069 A    12/1968  Decupper
3,576,593 A    4/1971   Cicirello
(Continued)

FOREIGN PATENT DOCUMENTS

WO    0129535 A1    4/2001
WO    2009013507 A1    1/2009

OTHER PUBLICATIONS

International Search Report for PCT/US2011/021397, dated Oct. 27, 2011.
(Continued)

*Primary Examiner* — David Porta
*Assistant Examiner* — Djura Malevic
(74) *Attorney, Agent, or Firm* — Warner Norcross + Judd LLP

(57) ABSTRACT

Field balancing may be performed with an irradiation system including a plurality of adjustable radiant-energy emitters. The irradiation system powers the radiant-energy emitters from a power source and radiant energy is emitted from the radiant-energy emitters, where an amount of radiant energy emitted from each emitter is capable of being varied based on power received from the power source. A plurality of radiant-energy sensors detects an amount of radiant energy which includes radiant energy created directly by at least one of the radiant-energy emitters. The amount of radiant energy detected at at least two of the radiant-energy sensors is compared, and at least one of the radiant-energy emitters is adjusted by varying the power received from the power source so that the amount of radiant energy detected at each of the radiant-energy sensors tends towards becoming approximately equal. The emitting of radiant energy from each radiant-energy emitter is terminated when a total amount of radiant energy emitted from the plurality of adjustable radiant-energy emitters exceeds a predetermined
(Continued)

threshold value, where the threshold value is sufficient to allow the total amount of radiant energy emitted from the plurality of adjustable radiant-energy emitters to sanitize a particular area in which the emitters are located.

25 Claims, 16 Drawing Sheets

Related U.S. Application Data continuation of application No. 13/006,870, filed on Jan. 14, 2011, now Pat. No. 8,455,832.

(60) Provisional application No. 61/295,016, filed on Jan. 14, 2010, provisional application No. 61/362,955, filed on Jul. 9, 2010.

(51) Int. Cl.
*G01J 1/42* (2006.01)
*A61L 2/00* (2006.01)
*A61L 9/20* (2006.01)
*C02F 1/32* (2006.01)

(52) U.S. Cl.
CPC ............ *G01J 1/429* (2013.01); *G01J 1/4228* (2013.01); *C02F 1/32* (2013.01); *C02F 2201/326* (2013.01)

(58) Field of Classification Search
USPC .......................................... 250/461.1, 354.1
See application file for complete search history.

(56) References Cited

U.S. PATENT DOCUMENTS

| | | | |
|---|---|---|---|
| 3,674,421 A | 7/1972 | Decupper | |
| 4,158,493 A | 6/1979 | Fohl et al. | |
| 4,368,966 A | 1/1983 | Hagyuda | |
| 4,432,630 A * | 2/1984 | Haas | ................... 355/1 |
| 4,458,995 A | 7/1984 | Ishida et al. | |
| 4,786,812 A | 11/1988 | Humphreys | |
| 4,896,042 A | 1/1990 | Humphreys | |
| 4,910,942 A * | 3/1990 | Dunn | ................ A23L 3/005 53/425 |
| 5,129,928 A | 7/1992 | Chan et al. | |
| 5,422,702 A * | 6/1995 | Yasukawa | ................ G03B 7/16 396/157 |
| 5,434,419 A * | 7/1995 | Decupper | ................ A61L 2/24 250/372 |
| 5,446,289 A * | 8/1995 | Shodeen | ................ A61L 2/10 250/453.11 |
| 5,656,096 A | 8/1997 | Van Alstyne | |
| 5,721,971 A | 2/1998 | Sasaki | |
| 5,788,940 A * | 8/1998 | Cicha | ................ B65B 55/08 250/455.11 |
| 5,878,283 A | 3/1999 | House et al. | |
| 5,891,399 A | 4/1999 | Owesen | |
| 5,920,075 A * | 7/1999 | Whitehead | ................ A61L 2/10 250/492.1 |
| 5,925,885 A * | 7/1999 | Clark | ................ A23L 3/26 250/455.11 |
| 5,996,155 A * | 12/1999 | Chao | ................ A61L 2/10 68/13 R |
| 6,031,999 A | 2/2000 | Ogawa | |
| 6,656,096 B2 | 12/2003 | Sela | |
| 6,656,424 B1 | 12/2003 | Deal | |
| 6,798,341 B1 | 9/2004 | Eckel et al. | |
| 6,911,177 B2 | 6/2005 | Deal | |
| 7,175,806 B2 * | 2/2007 | Deal | ................ A61L 2/10 250/455.11 |
| 7,502,568 B1 | 3/2009 | Mohan | |
| 7,545,969 B2 | 6/2009 | Bennett et al. | |
| 7,829,016 B2 | 11/2010 | Deal et al. | |
| 7,859,194 B2 | 12/2010 | Walker et al. | |
| 8,067,750 B2 * | 11/2011 | Deal | ................ A61L 2/10 250/453.11 |
| 8,154,650 B2 | 4/2012 | Tsai | |
| 8,455,832 B2 | 6/2013 | Statham et al. | |
| 2002/0004995 A1 * | 1/2002 | France | ................ B01D 15/00 34/524 |
| 2002/0146343 A1 * | 10/2002 | Jenkins | ................ A61L 2/24 422/24 |
| 2002/0178343 A1 * | 11/2002 | Tsai | ................ G06F 1/1626 712/1 |
| 2002/0187253 A1 * | 12/2002 | Marcus | ................ C23C 14/12 427/8 |
| 2003/0001959 A1 | 6/2003 | Tanaka et al. | |
| 2004/0120844 A1 * | 6/2004 | Tribelsky et al. | ............... 422/2 |
| 2004/0169854 A1 | 9/2004 | Vo-Dinh et al. | |
| 2004/0256581 A1 | 12/2004 | Au et al. | |
| 2005/0051466 A1 * | 3/2005 | Carter et al. | ................... 210/94 |
| 2005/0242013 A1 | 11/2005 | Hunter et al. | |
| 2005/0243198 A1 * | 11/2005 | Pardikes | ................ G03B 15/05 348/370 |
| 2006/0076048 A1 | 4/2006 | Gaudiana et al. | |
| 2006/0133643 A1 | 6/2006 | Bennett et al. | |
| 2007/0151905 A1 | 7/2007 | Wang et al. | |
| 2007/0187626 A1 | 8/2007 | Gaska et al. | |
| 2007/0287091 A1 | 12/2007 | Jacobo et al. | |
| 2007/0291466 A1 * | 12/2007 | Krestakos | .............. H04N 7/142 362/33 |
| 2008/0075629 A1 | 3/2008 | Deal et al. | |
| 2008/0211420 A1 | 9/2008 | Walker et al. | |
| 2009/0008372 A1 * | 1/2009 | Lee | ................ B08B 7/0042 219/121.68 |
| 2009/0048648 A1 | 2/2009 | Dacey, Jr. et al. | |
| 2009/0095906 A1 * | 4/2009 | Gavner | ............. H04N 1/00307 250/338.1 |
| 2010/0112945 A1 | 5/2010 | Hanif | |
| 2010/0151957 A1 * | 6/2010 | Hohla et al. | ................ 473/221 |
| 2010/0238344 A1 | 9/2010 | Tsai | |
| 2010/0265690 A1 * | 10/2010 | Portmann et al. | ................ 362/6 |
| 2011/0074946 A1 * | 3/2011 | Lechocinski et al. | ........ 348/135 |
| 2011/0075144 A1 * | 3/2011 | Lechocinski et al. | ........ 356/364 |
| 2011/0214686 A1 * | 9/2011 | Chavana, Jr. | ............. A47L 9/00 134/1 |
| 2012/0126134 A1 * | 5/2012 | Deal | ................ A61L 2/10 250/372 |
| 2012/0274775 A1 * | 11/2012 | Reiffel | ................ 348/158 |

OTHER PUBLICATIONS

Extended European Search Report for Application No. 11733483.9, dated May 4, 2017, 9 pages.

* cited by examiner

SYSTEMS AND METHODS FOR EMITTING RADIANT ENERGY

CROSS-REFERENCE TO RELATED APPLICATIONS

This application is a continuation of U.S. application Ser. No. 13/877,684 filed May 6, 2013, which is a continuation of U.S. application Ser. No. 13/006,870 filed Jan. 14, 2011, now U.S. Pat. No. 8,455,832, which, in turn, claims the benefit of U.S. provisional Application No. 61/295,016 filed Jan. 14, 2010 and U.S. provisional Application No. 61/362,955 filed Jul. 9, 2010, the disclosures of which are incorporated in their entirety by reference herein.

TECHNICAL FIELD

The present disclosure generally relates to radiant-energy emission.

BACKGROUND

Illumination of surfaces with radiant energy has been used in surface treatments such as treatments related to curing, polymerization, oxidation, purification, disinfection, and sterilization. Generally, radiant energy is the energy of electromagnetic waves. The electromagnetic waves typically are classified into types according to the frequency of the electromagnetic waves. These types include (in order of increasing frequency): radio waves, microwaves, terahertz radiation, infrared radiation, visible light, ultraviolet light, X-rays, and gamma rays. Examples of such surface treatments include irradiating a surface with radiant energy to polymerize monomers to create a polymer coating on the surface. A surface may be irradiated with radiant energy to cure or crosslink a polymer on the surface. It is also known to irradiate a surface with radiant energy to disinfect or sterilize the surface.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every figure. The drawings are not necessarily to scale, emphasis instead being placed upon illustrating embodiments, principles, and concepts.

DETAILED DESCRIPTION

Figure 1:
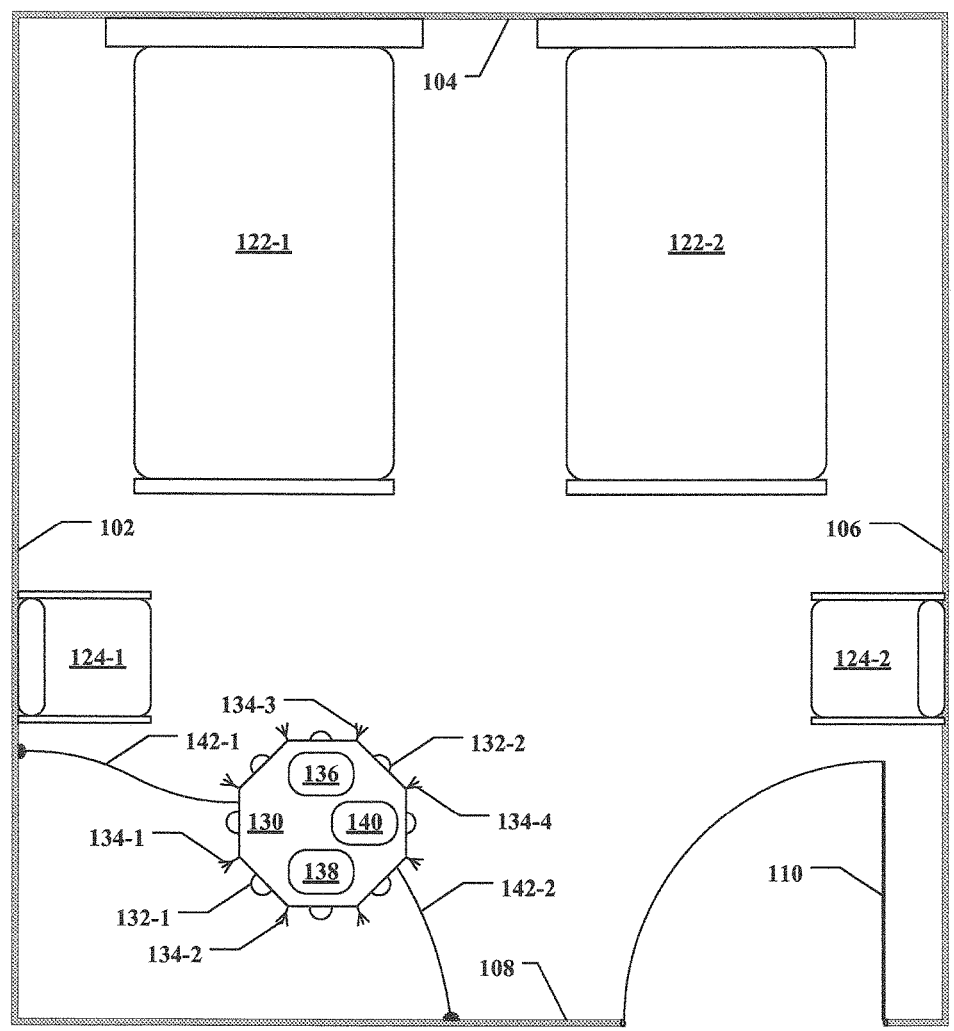
FIG. 1 shows a block diagram of a room treatable in accordance with an example embodiment of an irradiation system.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

One of the challenges of conventional approaches to automating the disinfection of room air and surfaces includes the distribution of UV-C in an efficient and effective manner. UV-C is a high frequency wavelength of light within the ultraviolet band shown to be bactericidal. UV-C has wavelengths of from about 100 nanometers to about 280 nanometers. Treatment time can be critical for commercial applications of automating such disinfection. A thorough and ubiquitous treatment of the room air and surfaces may be required for a process improvement over manual methods. The total amount of UV-C that is available for irradiating an area is typically limited by the amount of power available to make UV-C from standard electrical commercial and residential building circuits. Health care facilities are generally limited to a standard 20 Amp service and other facilities may have either 15 or 20 amp service. A system that does not manage the available power will almost assuredly waste UV-C output and prolong treatment time.

A number of conventional approaches to disinfecting an area by irradiating the area with UV-C are known in the art. A first conventional approach to irradiating an area includes manually positioning lamps and measuring lamp output in target locations in order to ensure that a desired germicidal dose is achieved. This first conventional approach reduces and may minimize the required treatment time. However, this first conventional approach may require a significant amount of setup time due to the manual positioning of lamps.

A second conventional approach to irradiating an area includes arbitrary lamp positioning. This second conventional approach reduces setup time because of the arbitrary positioning of lamps. However, this second conventional approach typically requires an overwhelming dose of UV-C to achieve disinfection because the lamps are frequently not positioned in optimum locations. Such an overwhelming dose of UV-C may be impractical due to high lamp output requirements or an extended treatment time requirement.

A third convention approach to irradiating an area includes arbitrary lamp positioning in conjunction with a reflectance-based endpoint detection. The endpoint can be detected using directional reflectance-only sensors to detect a cumulative amount of reflected UV-C. The UV-C reflectance may be read continuously until a predetermined amount of reflected UV-C is measured in one or more treatment zones. This third conventional approach makes more efficient use of power and time resources than the second conventional approach. However, the third conventional approach makes less efficient use of power and time resources than the first conventional approach.

Subject matter disclosed herein deviates from and improves upon conventional approaches to irradiating an area. Embodiments of the subject matter disclosed herein provide methods usable for irradiating an area with radiant energy. In a first particular embodiment, a method is performed by an irradiation system. The irradiation system emits radiant energy from each adjustable radiant-energy emitter of a plurality of adjustable radiant-energy emitters. The irradiation system detects an amount of radiant energy at each radiant-energy sensor of a plurality of radiant-energy sensors. The radiant energy detected at each radiant-energy sensor of the plurality of radiant-energy sensors is the UV-C field strength created by the radiant-energy emitters. The irradiation system adjusts each adjustable radiant-energy emitter of the plurality of adjustable radiant-energy emitters until the amount of radiant energy detected at each radiant-energy sensor of the plurality of radiant-energy sensors is approximately equal.

In particular embodiments, each adjustable radiant-energy emitter emits an adjustable flux or radiant energy during operation of the irradiation system. The irradiation system may adjust an adjustable radiant-energy emitter by adjusting the adjustable flux of radiant energy emitted by the adjustable radiant-energy emitter. In particular embodiments, the position of each adjustable radiant-energy emitter is adjustable. Repositioning an adjustable radiant-energy emitter may change the general direction in which the adjustable radiant-energy emitter emits radiant energy. The irradiation system may adjust the adjustable radiant-energy emitter by adjusting the position of the adjustable radiant-energy emitter. In particular embodiments, a radiant-energy emitter may include an adjustable reflector to reflect emitted radiant energy in a particular direction. Adjusting the adjustable reflectors may change the particular direction in which the adjustable radiant-energy emitter emits radiant energy. The irradiation system may adjust a radiant-energy emitter by adjusting the adjustable reflector to change the particular direction of the emitted radiant energy.

Embodiments of the subject matter disclosed herein provide computer-readable media including instructions that, when executed, enable an apparatus to perform methods usable for irradiating an area with radiant energy. In a second particular embodiment, the methods include the method described above with respect to the first particular embodiment.

Embodiments of the subject matter disclosed herein provide systems and apparatuses usable for irradiating an area. In a third particular embodiment, an apparatus comprises a plurality of radiant-energy emitters, a plurality of radiant-energy sensors, and control logic. Each radiant-energy emitter of the plurality of radiant-energy emitters emits an adjustable flux of radiant energy during operation of the apparatus. The radiant energy includes ultraviolet light having a wavelength in a range from about 100 nanometers to about 280 nanometers (UV-C). Each radiant-energy sensor of the plurality of radiant-energy sensors detects an amount of radiant energy during operation of the apparatus. The amount of radiant energy detected at each radiant-energy sensor of the plurality of radiant-energy sensors is the UV-C field strength that is created by the radiant-energy emitters and primarily includes direct radiant energy from at least one radiant-energy emitter of the plurality of radiant-energy emitters. The control logic adjusts the adjustable flux of radiant energy emitted from each of the plurality of radiant-energy emitters during operation of the apparatus until the amount of radiant energy detected at each of the plurality of radiant-energy sensors is approximately equal.

The control logic terminates emitting of the radiant energy from each radiant-energy emitter of the plurality of radiant-energy emitters when a total amount of radiant energy emitted from the plurality of radiant-energy emitters during operation of the apparatus exceeds a threshold value that is substantially sufficient to allow the total amount of radiant energy emitted from the plurality of radiant-energy emitters to sanitize a particular area in which the apparatus is located. Sanitizing a particular area may include disinfecting one or more surfaces in the particular area. Sanitizing a particular area may include sterilizing one or more surfaces in the particular area. In particular embodiments, sanitizing includes disinfecting at least one surface in the particular area and sterilizing at least one surface in the particular area.

FIG. 1 shows a block diagram of a room 100 treatable in accordance with an example embodiment of an irradiation system 130. The room 100 may include a left wall 102, a rear wall 104, a right wall 106, a front wall 108, a door 110, two beds (collectively 122), two chairs (collectively 124), and an irradiation system 130. In particular embodiments, the room 100 is a hospital room. In particular embodiments, the irradiation system may be mobile for adjustable positioning within the room 100. The irradiation system 130 may include eight adjustable radiant-energy emitters (collectively 132), two of which are labeled in FIG. 1. The irradiation system 130 also may include eight radiant-energy sensors (collectively 134), four of which are labeled in FIG. 1. In particular embodiments, the adjustable radiant-energy emitters 132 include a low-pressure mercury amalgam lamp. In particular embodiments, the adjustable radiant-energy emitters 132 emit UV-C.

In particular embodiments, the radiant-energy sensors 134 include a wide-angle cosine-corrected UV-C probe. Cosine corrected sensors are designed to detect UV-C in a 60 degree window in order to measure UV-C fluence within the window, ensuring the measurement of direct radiant energy. In particular embodiments, the irradiation system includes sixteen adjustable radiant-energy emitters 132 (200 Watts each) and eight radiant-energy sensors 134 (Cosine Corrected High Sensitivity, UV-C specific). In particular embodiments, the radiant-energy sensors 134 are photo-diodes filtered for the detection of only UV-C wavelengths. In particular embodiments, cosine correction may be achieved by using a TEFLON® filter that fits over the photo-diode. In particular embodiments, the radiant-energy sensors 134 are positioned above and forward of every other radiant-energy emitter 132, and protrude into the room 100 to achieve wide angle detection. In particular embodiments, the radiant-energy sensors 134 may be angled to face down 1-3 degrees in order to improve the collection of primary field radiant energy from the radiant-energy emitters 132.

The irradiation system 130 may also include a hygrometer 140. The irradiation system 130 may further include control logic (not shown), a power component 136, a battery pack 138, and two power cords (collectively 142). The control logic may control the operation of the irradiation system 130 and may include both hardware and software. For example, the control logic may include a processor, memory, and circuitry that connects the processor to the memory and to other components of the irradiation system 130. The memory may include instructions that, when executed by the processor, enables the irradiation system 130 to perform operations described herein.

During operation, the power component 136 receives electrical power from one or more power sources and uses the received electrical power to power the irradiation system 130. The amount of power available from a single power circuit can limit the flux of radiant energy that can be emitted from the irradiation system 130. Thus, the power component 136 is designed to be able to receive electrical power from a plurality of power sources. For example, the power cords 142 may be connected to two different power circuits (i.e., two different power sources). The battery pack 138 may be an additional source of electrical power to the power component 136. When the power component 136 receives electrical power from a plurality of power sources, the irradiation system 130 can emit more radiant energy in a particular amount of time than when the power component 136 receives electrical power from a single power source. When the power component 136 receives electrical power from a plurality of power sources, the irradiation system 130 can emit the same amount of radiant energy in a shorter amount of time than when the power component 136 receives electrical power from a single power source. The single power source may be a single power cord 142 connected to a single power circuit. Also, the single power source may be the battery pack 138.

Each adjustable radiant-energy emitter 132 of the plurality of adjustable radiant-energy emitters 132 emits an adjustable flux of radiant energy during operation of the irradiation system 130. Each radiant-energy sensor 134 of the plurality of radiant-energy sensors 134 detects radiant energy during the operation of the irradiation system 130. The radiant energy detected at each radiant-energy sensor 134 is the UV-C field created by the radiant-energy emitters 132 and primarily includes an amount of radiant energy directly from at least one adjustable radiant-energy emitter 132 of the plurality of adjustable radiant-energy emitters 132. Each radiant-energy sensor 134 may also receive radiant energy from other radiant-energy emitters 132 and radiant energy from other sources. For example, each radiant-energy sensor 134 may receive radiant energy that has been reflected off of the walls 102, 104, 106, 108, furniture 122, 124 in the room 100, or off of any device itself, for example. In this embodiment, however, there is no mechanism to measure the radiant energy from a primary radiant-energy emitter, a secondary radiant-energy emitter, any reflected radiant energy, or the source of the reflected radiant energy. The radiant-energy sensors 134 detect the strength of the entire radiant energy field created primarily by the radiant-energy emitters 132 directly so that the irradiation system 130 may adjust the radiant-energy emitters 132 to balance the field through the use of control logic. The control logic may adjust each of the plurality of adjustable radiant-energy emitters 132 during operation of the irradiation system 130 until the amount of radiant energy detected at each radiant-energy sensor is approximately equal. The control logic may adjust an adjustable radiant-energy emitter 132 by 1) adjusting the adjustable flux of radiant energy emitted from the adjustable radiant-energy emitter 132, 2) adjusting the position of the adjustable radiant-energy emitter 132, or 3) by adjusting a reflector at the adjustable radiant-energy emitter 132.

The adjustment of each adjustable flux may emulate the movement of an adjustable radiant-energy emitter 132 closer to an area of the room 100 or emulate the movement of an adjustable radiant-energy emitter 132 further from an area of the room 100. For example, a first adjustable radiant-energy emitter 132-1 may be emitting more radiant energy than is needed because of the proximity of the left wall 102 and the front wall 108 to the adjustable radiant-energy emitter 132-1. A second adjustable radiant-energy emitter 132-2 may not be emitting a sufficient amount of radiant energy because of the distance of the rear wall 104 and the right wall 106 from the radiant-energy emitter 132-2. That is, the radiant energy emitted from the first adjustable radiant-energy emitter 132-1 is being applied to a smaller area than the area to which the radiant energy emitted from the second adjustable radiant-energy emitter 132-2 is being applied. Additionally, there are objects (e.g., first bed 122-1, second bed 122-2, and second chair 124-2) in the general area to which the radiant energy emitted from the second adjustable radiant-energy emitter 132-2 is being applied. In particular embodiments, the amount of radiant energy detected at first radiant-energy sensor 134-1 and second radiant-energy sensor 134-2 will be greater than the amount of radiant energy detected at the third radiant-energy sensor 134-3 and the fourth radiant-energy sensor 134-4. The control logic may decrease the flux of radiant energy emitted from the first adjustable radiant-energy emitter 132-1, emulating a movement of the first radiant-energy emitter 132-1 away from that area. Similarly, the control logic may increase the flux of radiant energy emitted from the second adjustable radiant-energy emitter 132-2, emulating movement of the second adjustable radiant-energy emitter 132-2 toward that area.

The irradiation system 130 may continue adjusting the adjustable flux of radiant energy emitted from each adjustable radiant-energy emitter 132 until the amount of radiant energy detected at each radiant-energy sensor 134 is approximately equal. The adjusting of the adjustable fluxes may be referred to as field balancing. Similarly, the irradiation system 130 may continue to adjust the position of each radiant-energy emitter 132 or continue to adjust a reflector at each radiant-energy emitter 132 until the amount of radiant energy detected at each radiant-energy sensor 134 is approximately equal. It should be noted that, with the adjustment of radiant-energy emitters 132, more power may be used by a particular radiant-energy emitter 132 that is adjusted to emit radiant energy at a higher level or due to the radiant-energy emitter 132 being worn or not as effective as another radiant-energy emitter 132, for example. Adjusting the radiant-energy emitters 132 provides the ability to use the power available to reduce treatment times. In one embodiment, the power consumption is monitored and adjusting of the radiant-energy emitters 132 may be discontinued once the specified available power is reached. Irrespective of whether only a single power source is available or multiple power sources are available as described above, this adjustment of the radiant-energy emitters 132 acts to limit the treatment time for a particular target area.

In particular embodiments, the irradiation system 130 emits radiant energy from each of the adjustable radiant-energy emitters 132 until a total amount of radiant energy emitted from the adjustable radiant-energy emitters 132 reaches or exceeds a threshold value. When the total amount of radiant energy emitted reaches or exceeds the threshold value, the control logic may terminate the emitting of radiant energy from the adjustable radiant-energy emitters 132. In particular embodiments, the threshold value is sufficient to allow the total amount of radiant energy emitted from the adjustable radiant-energy emitters 132 to sanitize the room 100. In particular embodiments, the threshold value is sufficient to allow the total amount of radiant energy emitted from the adjustable radiant-energy emitters 132 to sterilize at least one surface in the room 100. In particular embodiments, the threshold value is sufficient to allow the total amount of radiant energy emitted from the adjustable radiant-energy emitters 132 to polymerize a coating on at least one surface in the room 100. In particular embodiments, the threshold value is sufficient to allow the total amount of radiant energy emitted from the adjustable radiant-energy emitters 132 to cure a polymer-based coating on at least one surface in the room 100. In particular embodiments, the threshold value is sufficient to allow the total amount of radiant energy emitted from the adjustable radiant-energy emitters 132 to oxidize at least one surface in the room 100.

In an example embodiment, after a warm-up phase, a baseline UV-C target value may be determined by taking the average of the radiant energy detected at each radiant-energy sensor 134 with all the radiant-energy emitters 132 set to 90% output. The control logic then attempts to match all the radiant energy values at the radiant-energy sensors 134 to the target value by adjusting the output of each radiant-energy emitter 132 up or down. In an example embodiment, the radiant-energy emitters may be adjusted in groups of three, with a primary radiant-energy emitter of the group immediately below one of the radiant-energy sensors 134, and secondary radiant-energy emitters on either side of the primary radiant-energy emitter.

Figure 2:
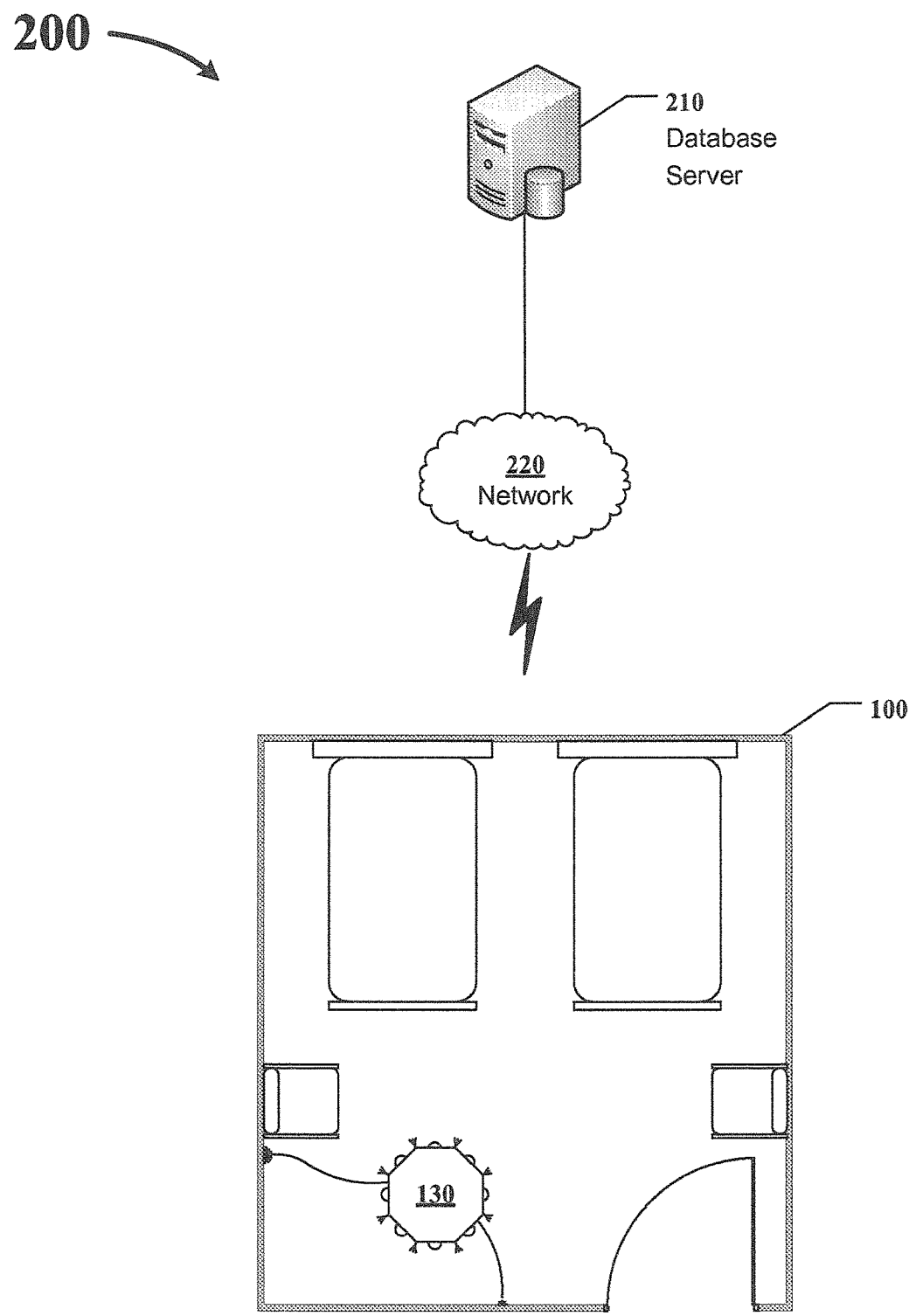
FIG. 2 shows a block diagram of an example embodiment of a quality-control system including the irradiation system shown in FIG. 1.

FIG. 2 shows a block diagram of an example embodiment of a quality-control system 200 including the irradiation system 130 shown in FIG. 1. The network 220 may include a wireless local area network (WLAN) or the Internet, for example. The irradiation system 130 may communicate wirelessly with the database server 210 via the network 220. In particular embodiments, the database server 210 is configured to store information received from the irradiation system 130 via the network 220.

The information received from the irradiation system 130 may include location information identifying the location to be irradiated with a total amount of radiant energy emitted from the adjustable radiant-energy emitters 132. The location information may include the room number (or other identifying indicia) of the room 100 to be irradiated. The location information may be provided to the irradiation system 130 by a user of the irradiation system 130. In particular embodiments, the irradiation system 130 includes a user interface allowing a user to manually enter the location information to be transmitted to the database server 210. In particular embodiments, the irradiation system 130 includes a bar code reader and the user can scan a bar code associated with the particular room to be irradiated. A bar code may be attached to the front wall 108 near the door 110, for example. In particular embodiments, the room 100 may include a radio frequency identification (RFID) tag that transmits a unique room identifier to the irradiation system 130 when the RFID tag is activated by the irradiation system 130. In particular embodiments, the irradiation system 130 may need to be communicating with the RFID tag in order to emit radiant energy. Requiring the irradiation system 130 to be communicating with the RFID tag to emit radiant energy may reduce or eliminate errors in the location information transmitted to the database server 210.

The information received from the irradiation system 130 may include information indicating a measure of relative humidity at the location of the irradiation system 130. High relative humidity can inhibit the germicidal effect of UV-C. In particular embodiments, the irradiation system 130 includes a hygrometer 140. The hygrometer 140 may be a digital hygrometer. In particular embodiments, the irradiation system 130 transmits a measure of relative humidity along with the location information described above.

After the irradiation system 130 transmits location information to the database server 210, the irradiation system 130 may receive operational information from the database server 210. In particular embodiments, the operational information includes the threshold value described above. The threshold value may be at least partially based on the location information transmitted to the database server 210. The threshold value may be at least partially based on relative humidity information transmitted to the database server 210. For example, upon receiving a particular room number from the irradiation system 130, the database server 210 may retrieve specific information related to the particular room. The specific information may include the size of the room, the shape of the room, an inventory of the furniture in the room, and the diagnosis of the last patient to be in the room (i.e., when the room is a hospital room), for example. The database server 210 may then use this specific information to determine an appropriate threshold value, and other operational information, to be transmitted to the irradiation system 130.

In particular embodiments, the other operational information is at least partially based on relative humidity information transmitted to the database server 210. The other operational information may include initial values for the adjustable flux of radiant energy to be emitted from each of the adjustable radiant-energy emitters 132 during operation of the irradiation system 130. In particular embodiments, the initial values for the adjustable fluxes are the final values of the adjustable fluxes at the end of a previous operation of the irradiation system 130 in the same room. This may help reduce power consumption in rooms where the irradiation system 130 is frequently placed in approximately the same position each time it is operated in a particular room. The other operational information may include initial positions for each of the adjustable radiant-energy emitters 132. In particular embodiments, the initial positions for the adjustable radiant-energy emitters 132 are the final positions of the adjustable radiant-energy emitters 132 at the end of a previous operation of the irradiation system 130 in the same room. The other operational information may include an initial position for each reflector at each adjustable radiant-energy emitter 132. In particular embodiments, the initial position for each reflector at each adjustable radiant-energy emitter 132 is the final position of the reflector at the end of a previous operation of the irradiation system 130 in the same room.

In particular embodiments, the irradiation system 130 collects operational information including information related to the emitting of radiant energy from the adjustable radiant-energy emitters 132, information related to the detecting of radiant energy at the radiant-energy sensors 134, information related to the adjusting of adjustable fluxes, information related to repositioning of adjustable radiant-energy emitters 132, and information related to adjusting of reflectors at adjustable radiant-energy emitters 132. The collected information may be transmitted to the database server 210 via the network 220. The irradiation system 130 may transmit collected information as it is collected during operation of the irradiation system 130. The irradiation system 130 may also save collected information during the operation of the irradiation system 130 and then transmit all the collected information near the end of the operation of the irradiation system 130. The collected operational information may include location identification (e.g., room number), an operation start time, an operation end time, initial values of the adjustable fluxes, interim values of the adjustable fluxes, final values of the adjustable fluxes, initial positions of adjustable radiant-energy emitters 132, final positions of radiant-energy emitters 132, initial positions of reflectors at adjustable radiant-energy emitters 132, final positions of reflectors at adjustable radiant-energy emitters 132, total amount of radiant energy emitted, or any combination thereof.

Figure 3:
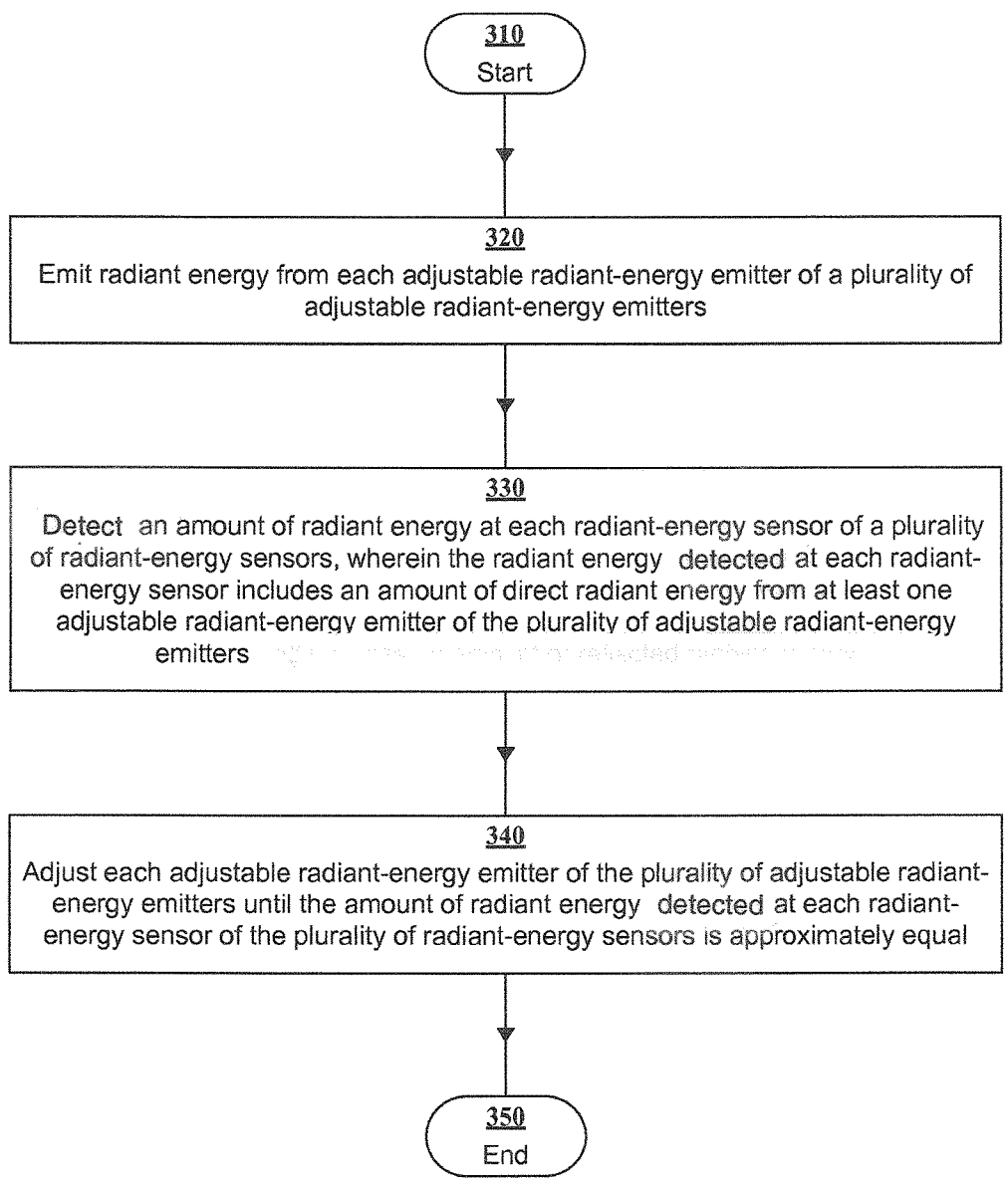
FIG. 3 shows a flow diagram of an example embodiment of a first method usable for irradiating an area.

In particular embodiments, the database server 210 includes software applications to perform quality control operations. For example, the database server 210 may receive the collected operational information from the irradiation system 130, store the collected operational information, and generate reports at least partially based on the collected operational data. In particular embodiments, the reports may be used to keep a history of operations to show compliance with certain regulations, such as government regulations. For example, guidance documents published by the Health and Human Services agency in the United States emphasize the importance of documenting the proper disinfection of health care facilities. A system, such as the quality-control system 200 shown in FIG. 2 may automate the documentation of disinfection of rooms in a healthcare facility. For example, the quality-control system 200 may be used to document which rooms were disinfected, when each room was disinfected, operation parameters depicting how each room was disinfected, which user was responsible for the disinfection of each room, or any combination thereof FIG. 3 shows a flow diagram of an example embodiment of a first method 300 usable for irradiating an area. The first method 300 may be performed by an irradiation system, such as the irradiation system 130 shown in FIGS. 1 and 2. Although the flow diagram indicates operations proceeding sequentially, an operation shown later in the sequence may be performed simultaneously with an operation shown earlier in the sequence. For example, operation 330 and operation 340 may be performed simultaneously.

The first method starts at 310. At 320, the irradiation system emits radiant energy from each adjustable radiant-energy emitter of a plurality of adjustable radiant-energy emitters.

At 330, the irradiation system detects an amount of radiant energy at each radiant-energy sensor of a plurality of radiant-energy sensors. The radiant energy detected at each radiant-energy sensor is the strength of the UV-C field and primarily includes an amount of direct radiant energy from at least one adjustable radiant-energy emitter that is disposed nearest the radiant-energy sensor's location.

At 340, the irradiation system adjusts each adjustable radiant-energy emitter of the plurality of adjustable radiant-energy emitters until the amount of radiant energy detected at each radiant-energy sensor of the plurality of radiant-energy sensors is approximately equal. The first method ends at 350.

Figure 4:
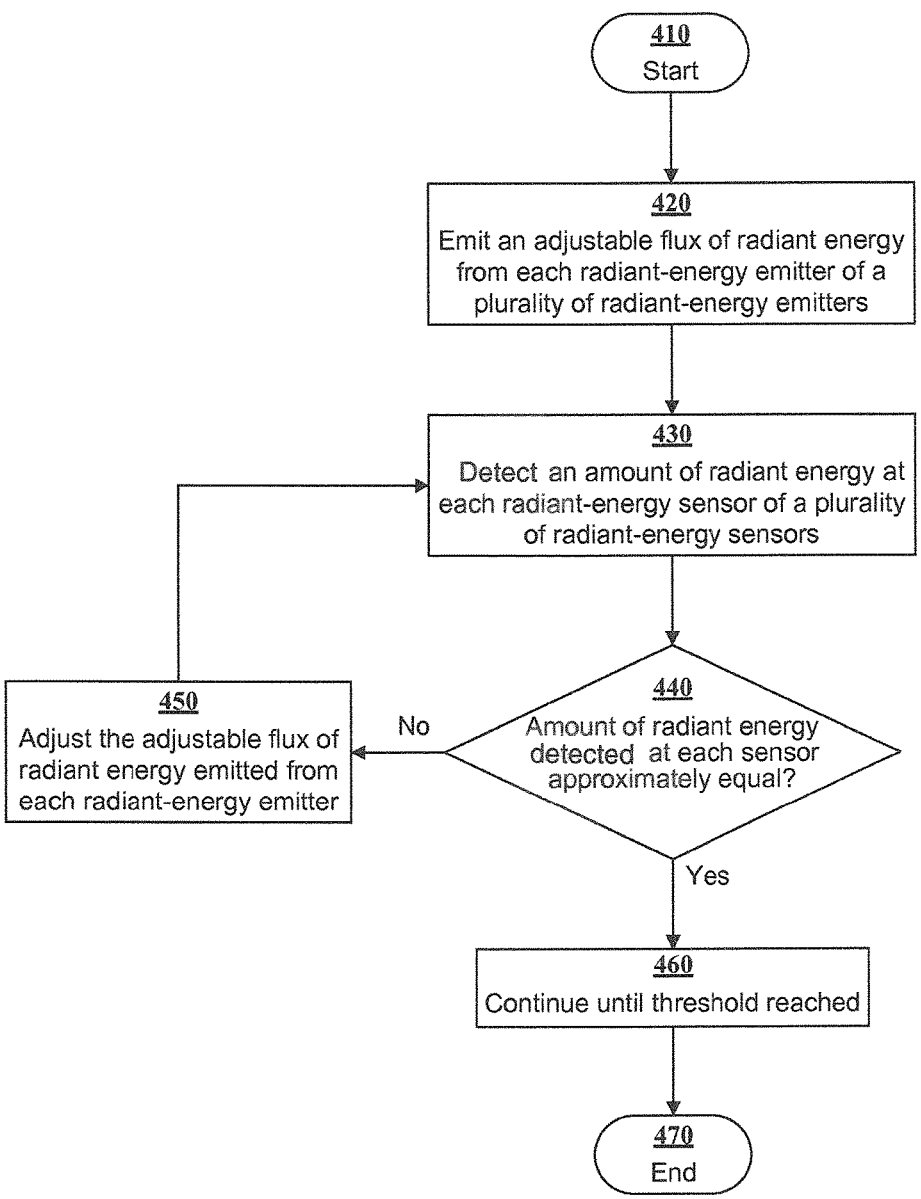
FIG. 4 shows a flow diagram of an example embodiment of a second method usable for irradiating an area.

FIG. 4 shows a flow diagram of an example embodiment of a second method 400 usable for irradiating an area. The second method 400 may be performed by an irradiation system, such as the irradiation system 130 shown in FIGS. 1 and 2.

The second method 400 begins at 410. At 420, the irradiation system emits an adjustable amount of flux of radiant energy from each radiant-energy emitter of a plurality of radiant-energy emitters.

At 430, the irradiation system detects an amount of radiant energy at each radiant-energy sensor of a plurality of radiant-energy sensors. At 440, the irradiation system determines whether the amount of radiant energy detected at each radiant-energy sensor is approximately equal.

If the radiant energy detected at each radiant-energy sensor is not approximately equal, the irradiation system proceeds to 450. If the radiant energy detected at each radiant-energy sensor of the plurality of radiant-energy sensors is approximately equal, the irradiation system proceeds to 460.

At 450, the irradiation system adjusts the adjustable flux of radiant energy emitted from each radiant-energy emitter. Adjusting the adjustable flux does not necessarily mean that the adjustable flux is changed. For example, the irradiation system may change the adjustable flux at seven of eight radiant-energy emitters and leave the adjustable flux the same at the eighth radiant-energy emitter. The adjustable flux at the eighth radiant-energy emitter is said to have been adjusted. Thus, adjusting an adjustable flux includes determining a new flux value. The new flux value may happen to be the same as the existing flux value.

At 460, the irradiation system continues emitting radiant energy until a threshold amount of radiant energy has been emitted by the irradiation system. The irradiation system may hold the adjustable fluxes constant once they are determined to be approximately equal or the irradiation system may periodically determine whether one or more of the adjustable fluxes as changed sufficiently to warrant adjusting the adjustable fluxes. At 470, the second method ends.

Figure 5:
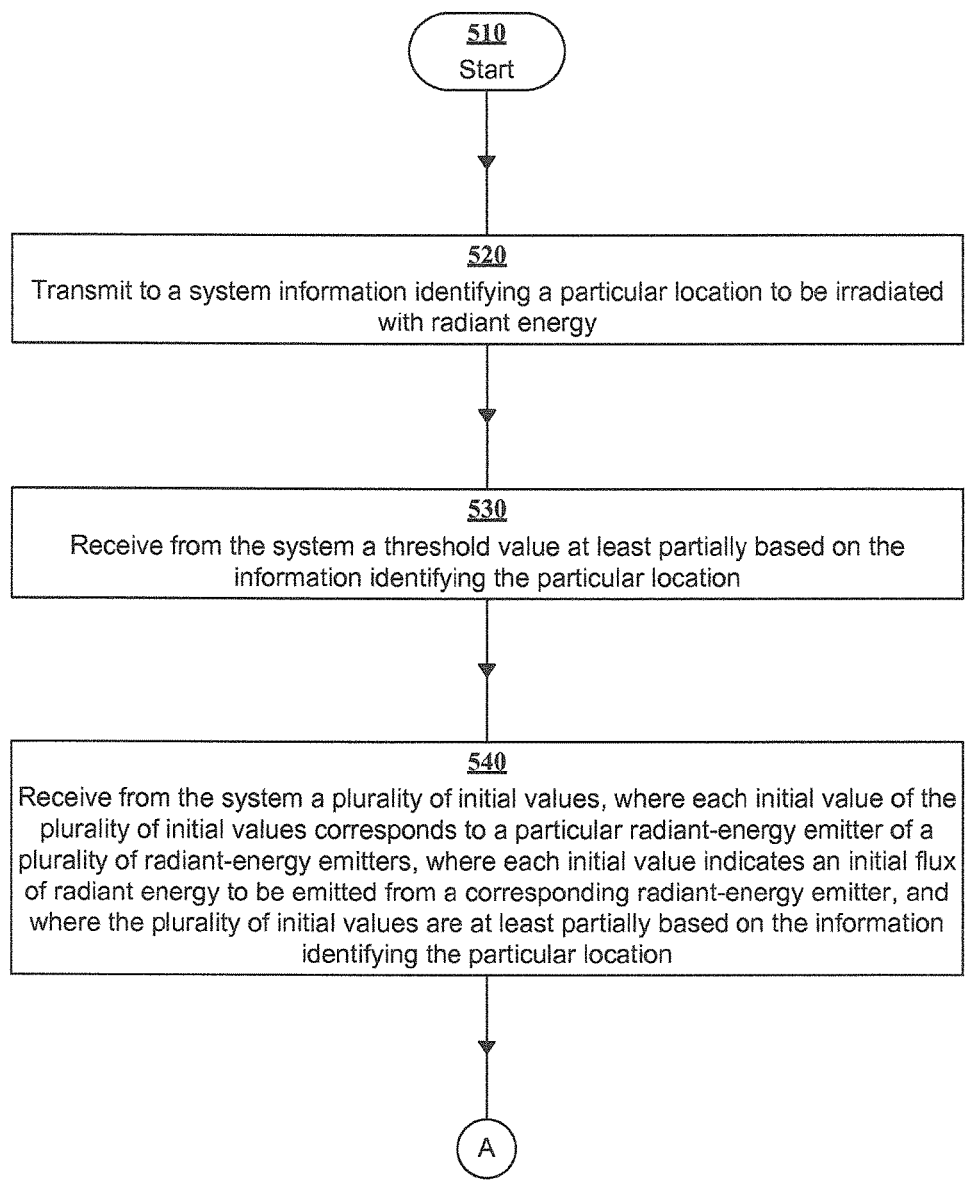
FIGS. 5-7 show a flow diagram of an example embodiment of a third method usable for irradiating an area.
Figure 6:
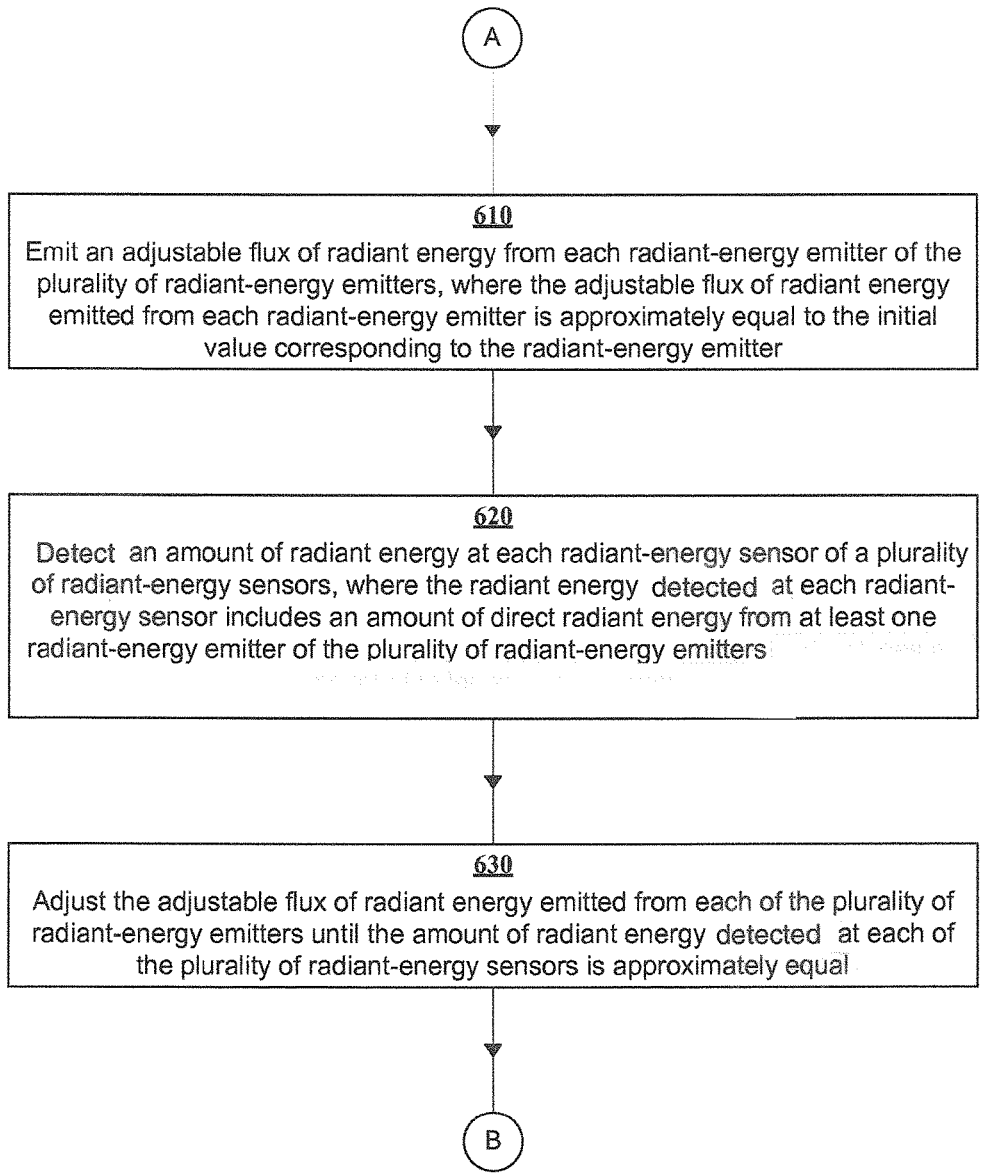
Figure 7:
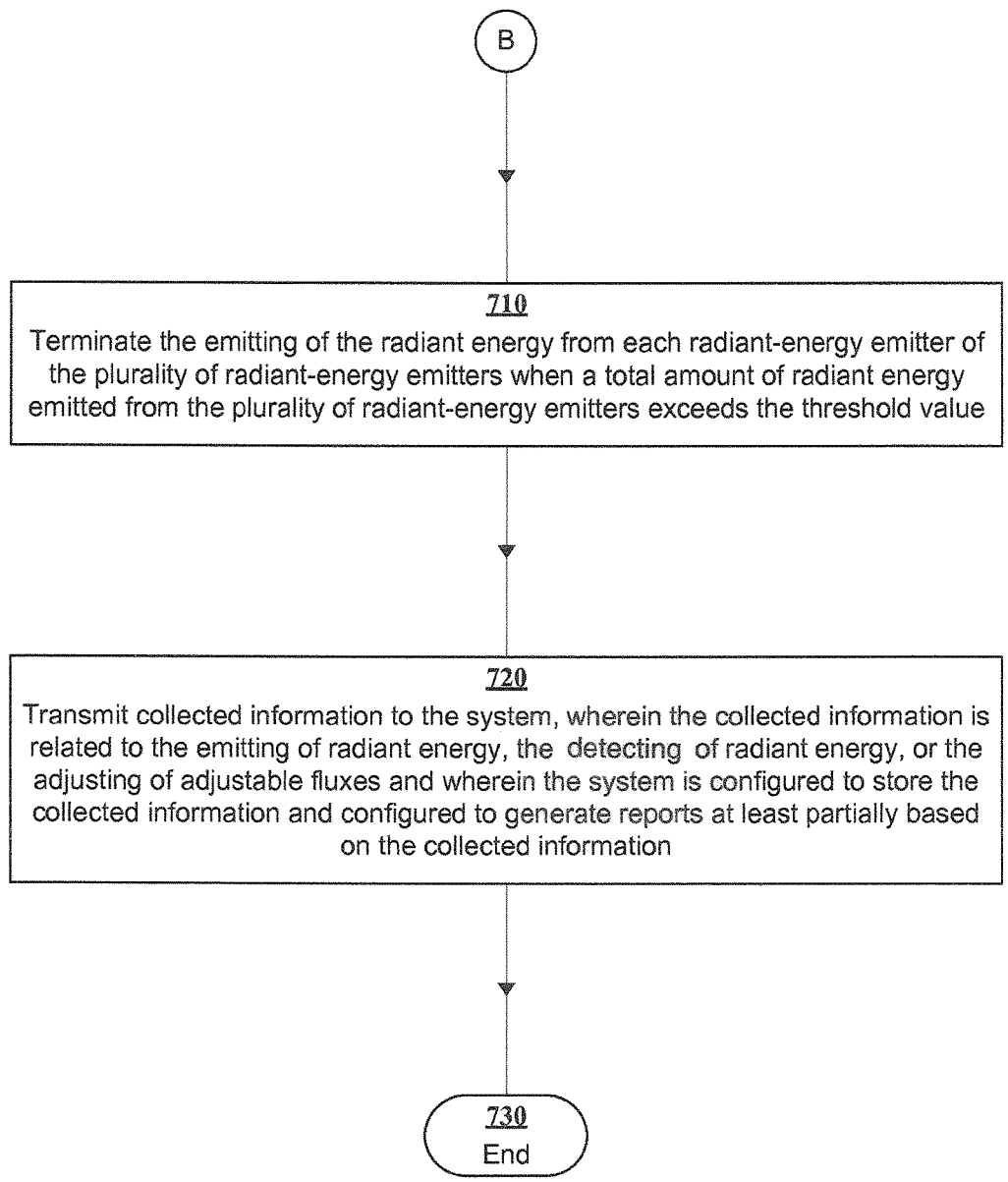

FIGS. 5-7 show a flow diagram of an example embodiment of a third method 500 usable for irradiating an area. The third method 500 may be performed by an irradiation system, such as the irradiation system 130 shown in FIGS. 1 and 2. Although the flow diagram indicates operations proceeding sequentially, an operation shown later in the sequence may be performed simultaneously with an operation shown earlier in the sequence. For example, operation 620 and operation 630 may be performed simultaneously. The third method 500 starts at 510.

At 520, the irradiation system transmits information to a system. The system may be the database server 210 shown in FIG. 2, for example. The transmitted information includes an identification of a particular location to be irradiated with radiant energy by the irradiation system. For example, the information may include the room number of the room 100 shown in FIGS. 1 and 2. At 530, the irradiation system receives a threshold value from the system. The threshold value is at least partially based on the information identifying the particular location to be radiated by the irradiation system.

At 540, the irradiation system receives a plurality of initial values from the system. Each initial value corresponds to a particular radiant-energy emitter of a plurality of radiant-energy emitters. Each initial value indicates an initial flux of radiant energy to be emitted from a corresponding radiant-energy emitter. Each initial value is at least partially based on the information identifying the particular location to be irradiated.

At 610, the irradiation system emits an adjustable flux of radiant energy from each radiant-energy emitter of the plurality of radiant-energy emitters. The adjustable flux or radiant energy emitted from each radiant-energy emitter is approximately equal to the initial value corresponding to the radiant-energy emitter.

At 620, the irradiation system detects an amount of radiant energy at each radiant-energy sensor of a plurality of radiant-energy sensors.

At 630, the irradiation system adjusts the adjustable flux of radiant energy emitted from each of the plurality of radiant-energy emitters until the amount of radiant energy detected at each of the plurality of radiant-energy sensors is approximately equal.

At 710, the irradiation system terminates the emitting of the radiant energy from each radiant-energy emitter of the plurality of radiant-energy emitters when a total amount of radiant energy emitted from the plurality of radiant-energy emitters exceeds the threshold value.

At 720, the irradiation system transmits collected information to the system. The collected information may include information related to the emitting of the radiant energy. The collected information may include information related to the detecting of the radiant energy. The collected information may include information related to the adjusting of the adjustable fluxes. The system to which the irradiation system transmits the collected information is configured to store the collected information and configured to generate reports at least partially based on the collected information. The third method 500 ends at 730.

Figure 8:
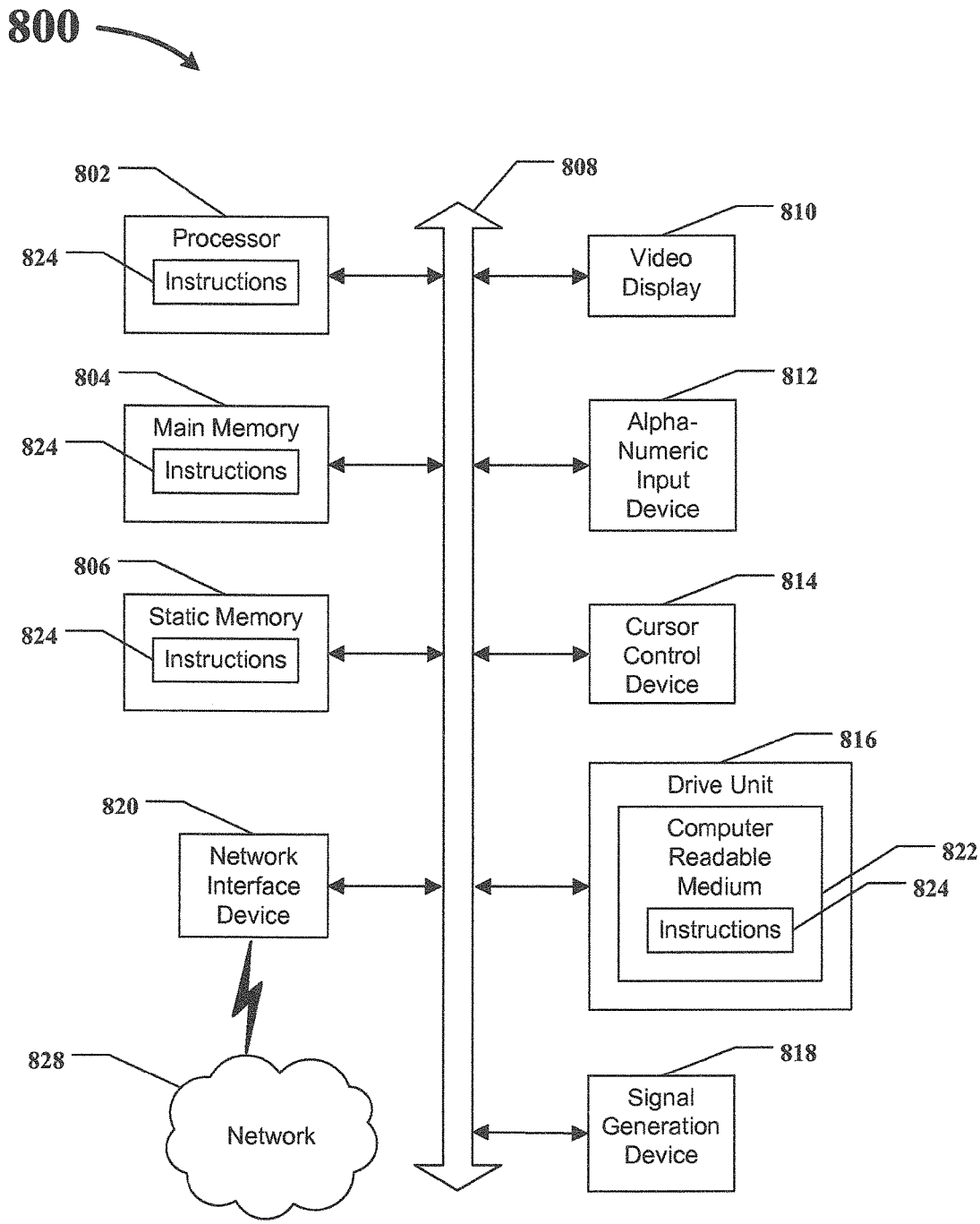
FIG. 8 shows a block diagram of an example embodiment of a general computer system.

FIG. 8 shows a block diagram of an example embodiment of a general computer system 800. The computer system 800 can include a set of instructions that can be executed to cause the computer system 800 to perform any one or more of the methods or computer-based functions disclosed herein. For example, the computer system 800 may include executable instructions to perform the methods discussed with respect to FIGS. 3-7. In particular embodiments, the computer system 800 includes executable instructions to implement the irradiation system 130 shown in FIGS. 1 and 2 or the database server 210 shown in FIG. 2. In particular embodiments, the computer system 800 includes or is included within the irradiation system 130 shown in FIGS. 1 and 2 or the database server 210 shown in FIG. 2. The computer system 800 may be connected to other computer systems or peripheral devices via a network, such as the network 220 shown in FIG. 2. Additionally, the computer system 800 may include or be included within other computing devices.

As illustrated in FIG. 8, the computer system 800 may include a processor 802, e.g., a central processing unit (CPU), a graphics processing unit (GPU), or both. Moreover, the computer system 800 can include a main memory 804 and a static memory 806 that can communicate with each other via a bus 808. As shown, the computer system 800 may further include a video display unit 810, such as a liquid crystal display (LCD), a projection television display, a flat panel display, a plasma display, or a solid state display. Additionally, the computer system 800 may include an input device 812, such as a remote control device having a wireless keypad, a keyboard, a microphone coupled to a speech recognition engine, a camera such as a video camera or still camera, or a cursor control device 814, such as a mouse device. The computer system 800 can also include a disk drive unit 816, a signal generation device 818, such as a speaker, and a network interface device 820. The network interface 820 enables the computer system 800 to communicate with other systems via a network 828. The network interface 820 may enable an irradiation system 130 to communicate with a database server 210 as shown in FIG. 2.

In a particular embodiment, as depicted in FIG. 8, the disk drive unit 816 may include a computer-readable medium 822 in which one or more sets of instructions 824, e.g. software, can be embedded. For example, the instructions 824 may embody one or more of the methods, such as the methods disclosed with respect to FIGS. 3-7, or logic as described herein. In a particular embodiment, the instructions 824 may reside completely, or at least partially, within the main memory 804, the static memory 806, and/or within the processor 802 during execution by the computer system 800. The main memory 804 and the processor 802 also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations, or combinations thereof.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing or encoding a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium.

Figure 9:
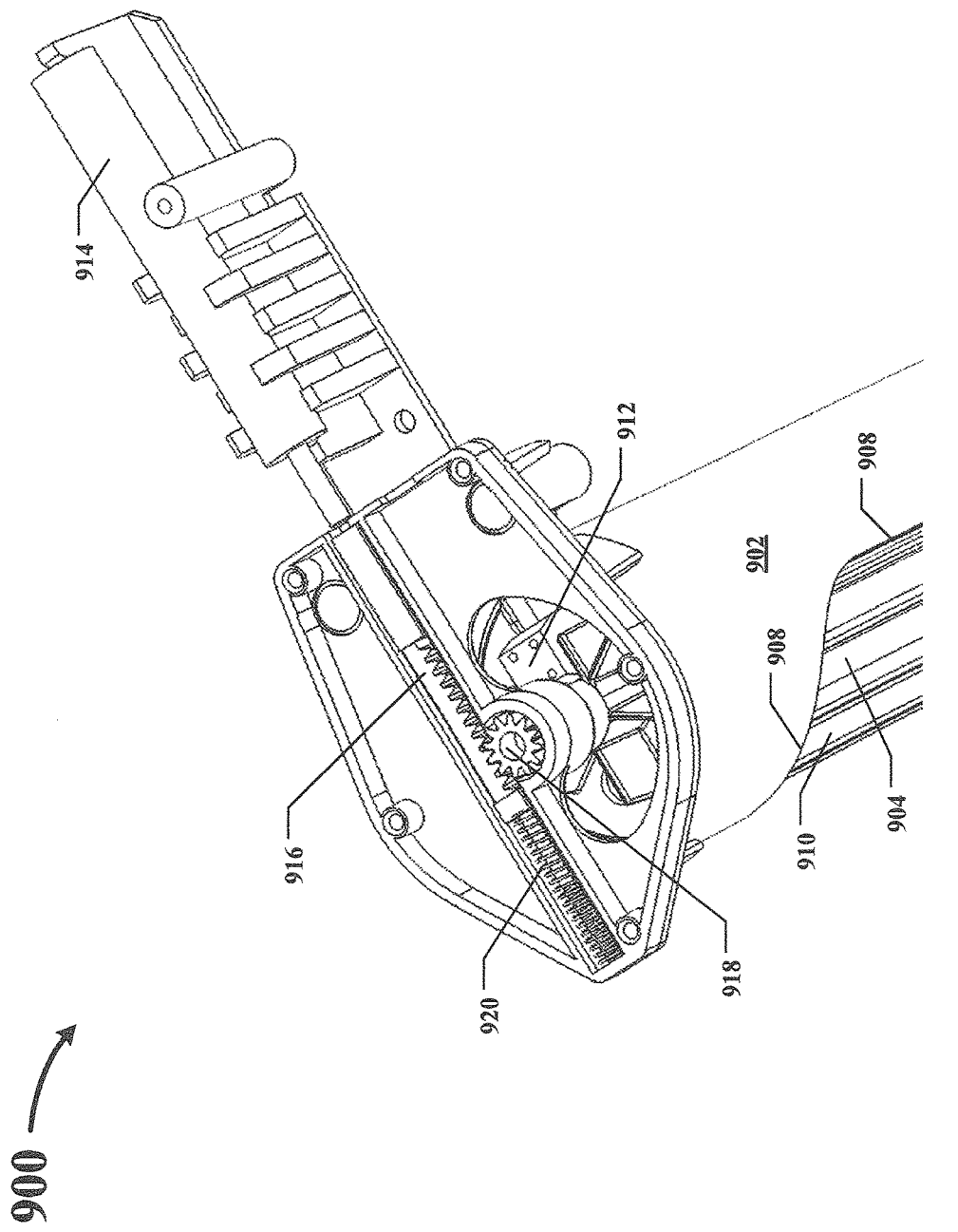
FIG. 9 shows a first perspective view of an example embodiment of a lamp module in a closed position.

FIG. 9 shows a first perspective view of an example embodiment of a lamp module 900 in a closed position. The lamp module 900 is usable in irradiation systems to emit UV-C. For example, the lamp module 900 may be included in the irradiation system 130 shown in FIGS. 1 and 2. The lamp module 900 may include a cylinder-shaped housing 902 that houses a D-shaped tube 904 and a UV-C lamp 906 (shown in FIGS. 10 and 12). In particular embodiments, the UV-C lamp 906 is an amalgam-type lamp. In particular embodiments, a UV-C-permeable sleeve made of quartz glass is used to maintain lamp temperature at lower power levels. In particular embodiments, the cylinder-shaped housing 902 and the D-shaped tube 904 are made of aluminum to increase reflection of UV-C. The cylinder-shaped housing 902 has a window 908 cut into one side of the cylinder-shaped housing 902 to expose either the rounded portion of the D-shaped tube 904 or the UV-C lamp 906, depending on whether the lamp module 900 is closed or opened. In FIG. 9, the lamp module 900 is in the closed position so that the rounded portion of the D-shaped tube 904 is exposed through the window 908 in the cylinder-shaped housing 902. The D-shaped tube 904 may include fins 910 on the rounded-portion of the D-shaped tube 904 to help provide rigidity to the D-shaped tube 904. The lamp module 900 includes a socket 912 into which the UV-C lamp 906 may be inserted to provide an electrical power source to the UV-C lamp 906.

The lamp module 900 includes a pneumatic cylinder 914, a rack gear 916, a pinion gear 918, and a spring 920. To emit UV-C from the lamp module 900, electrical power is supplied to the lamp module 900, activating the pneumatic cylinder 914 and the UV-C lamp 106. When the pneumatic cylinder 914 is activated it pushes the rack gear 916 away from the pneumatic cylinder 914, depressing the spring 920. The rack gear 916 engages the pinion gear 918, rotating the pinion gear 918 counter clockwise as shown in FIG. 9. The rotation of the pinion gear 918 causes the D-shaped tube 904 and the UV-C lamp 106 to rotate to the open position (shown in FIGS. 11 and 12).

Figure 10:
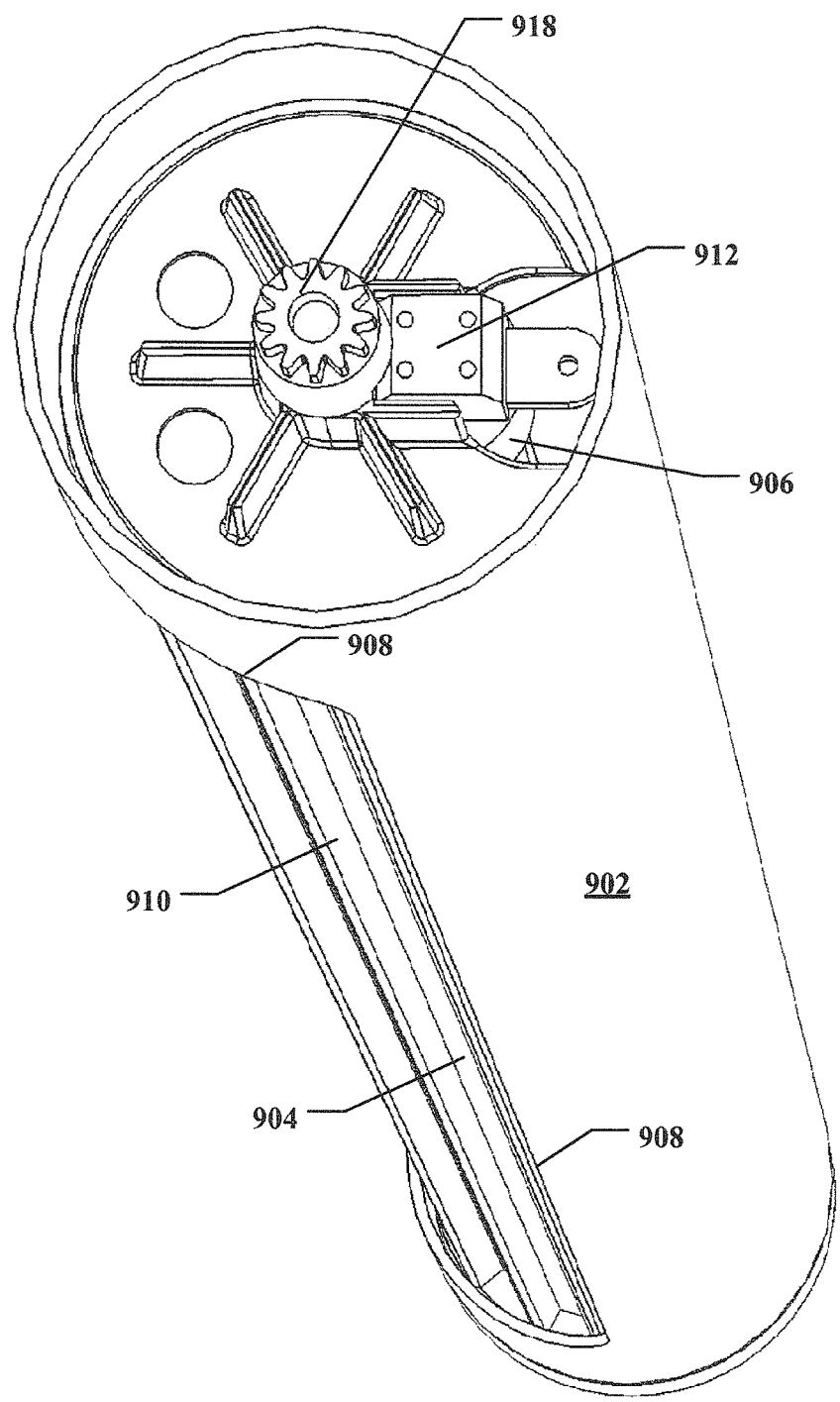
FIG. 10 shows a second perspective view of the example embodiment of the lamp module shown in FIG. 9 in a closed position.

FIG. 10 shows a second perspective view of the example embodiment of the lamp module 900 shown in FIG. 9 in a closed position. In FIG. 10, the top of the lamp module 900 has been removed. The top of the lamp module 900 includes the pneumatic cylinder 914, the rack gear 916, and the spring 920.

Figure 11:
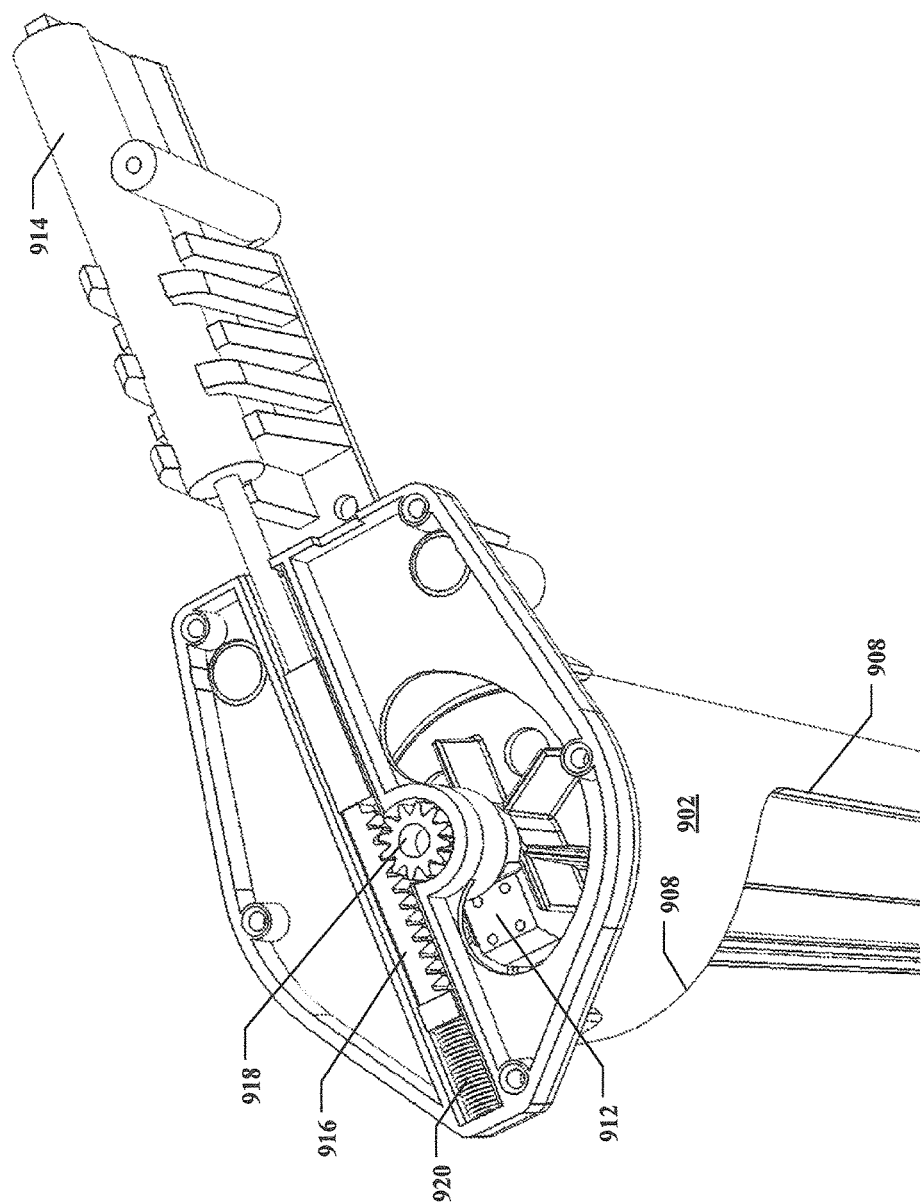
FIG. 11 shows a first perspective view of the example embodiment of the lamp module shown in FIG. 9 in an open position.

FIG. 11 shows a first perspective view of the example embodiment of the lamp module 900 shown in FIGS. 9 and 10 in an open position. In FIG. 11, the pneumatic cylinder 914 has been activated, pushing the rack gear 916 away from the pneumatic cylinder 914, rotating the pinion gear 918, and depressing the spring 920. The UV-C lamp 106 has been rotated to the open position exposing the UV-C lamp 906 through the window 908 in the cylinder-shaped housing 902. In the open position, the UV-C lamp 906 has electrical power supplied to it, causing it to emit UV-C. The amount of electrical power supplied to the UV-C lamp 906 may be adjusted to adjust the flux of the UV-C.

Figure 12:
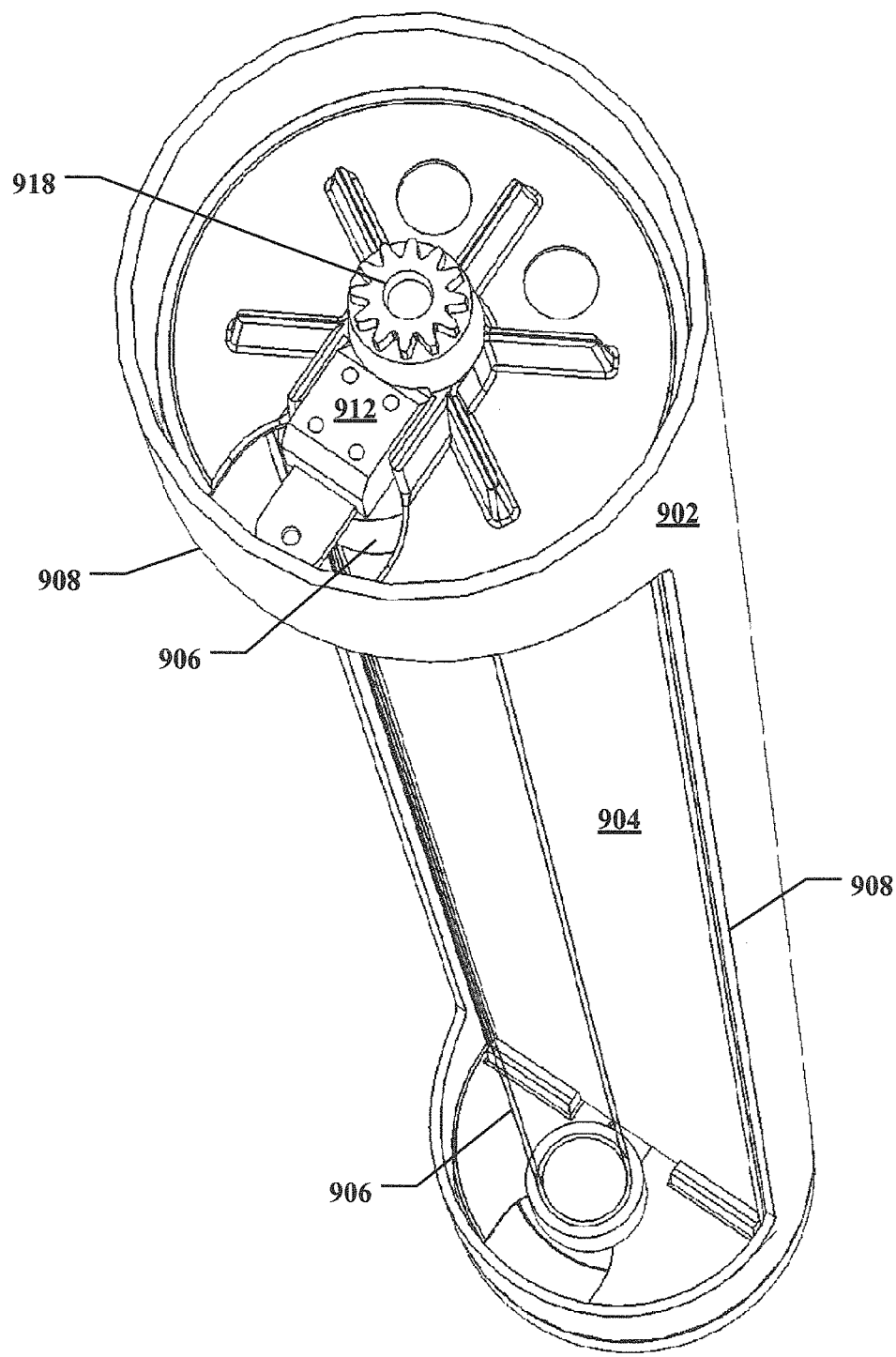
FIG. 12 shows a second perspective view of the example embodiment of the lamp module shown in FIG. 9 in an open position.

FIG. 12 shows a second perspective view of the example embodiment of the lamp module 900 shown in FIGS. 9, 10, and 11 in an open position. In FIG. 12, the top of the lamp module 900 has been removed. The top of the lamp module 900 includes the pneumatic cylinder 914, the rack gear 916, and the spring 920. The UV-C lamp 906 is rotated to the open position exposing the UV-C lamp 906 through the window 908 in the cylinder-shaped housing 902.

In the open position, the UV-C lamp 906 continues until an irradiation system including the lamp module 900 determines that UV-C no longer needs to be emitted. For example, the control logic of the irradiation system 130 shown in FIGS. 1 and 2 may determine that the threshold amount of UV-C has been emitted. The irradiation system 130 may shut off electrical power to the lamp module 900. Shutting off electrical power to the lamp module 900 causes the pneumatic cylinder 914 to deactivate and causes the UV-C lamp 106 to stop emitting UV-C. When the pneumatic cylinder 914 is deactivated, the spring 920 expands, pushing the rack gear 916 toward the pneumatic cylinder 914, which causes the pinion gear 918 to rotate clockwise as shown in FIG. 12. Rotating the pinion gear 918 clockwise causes the UV-C lamp 106 and the D-shaped tube 904 to rotate to the closed position shown in FIGS. 9 and 10.

Since users of an irradiation system including the lamp module 900 should not be exposed to the UV-C when the lamp module 900 is emitting UV-C, users will only be in close proximity to an irradiation system including the lamp module 900 when the lamp module 900 is in the closed position. In the closed position, the D-shaped tube 904 is exposed to the window 908 of the cylinder-shaped housing 902 an acts as a protective shield to shield the UV-C lamp 906 from damage. Damage may include breakage or contamination. Contamination may include contamination from fingerprints. The lamp module 900 may protect users from shattered glass or mercury contamination in the event of a shock sufficient to cause breakage through the cylinder-shaped housing 902 or the D-shaped tube 904. Although lamp module 900 is shown and described herein, it is understood that other lamp module configurations are also fully contemplated for use within irradiation system 130.

In particular embodiments, an irradiation system such as the irradiation system 130 shown in FIGS. 1 and 2 may include a protective shield that protects a plurality of radiant-energy emitters when the irradiation system is not emitting radiant energy. For example, when the irradiation system powers the radiant-energy emitters to emit radiant energy, the irradiation system may move the protective shield in order to expose the radiant-energy emitters to the area to be irradiated. When the irradiation system powers down the radiant-energy emitters, the irradiation system may move the protective shield to protect the radiant-energy emitters from exposure to the environment external to the irradiation system for the same reasons that a D-shaped tube 904 described above may be used to protect a radiant-energy emitter.

Figure 13:
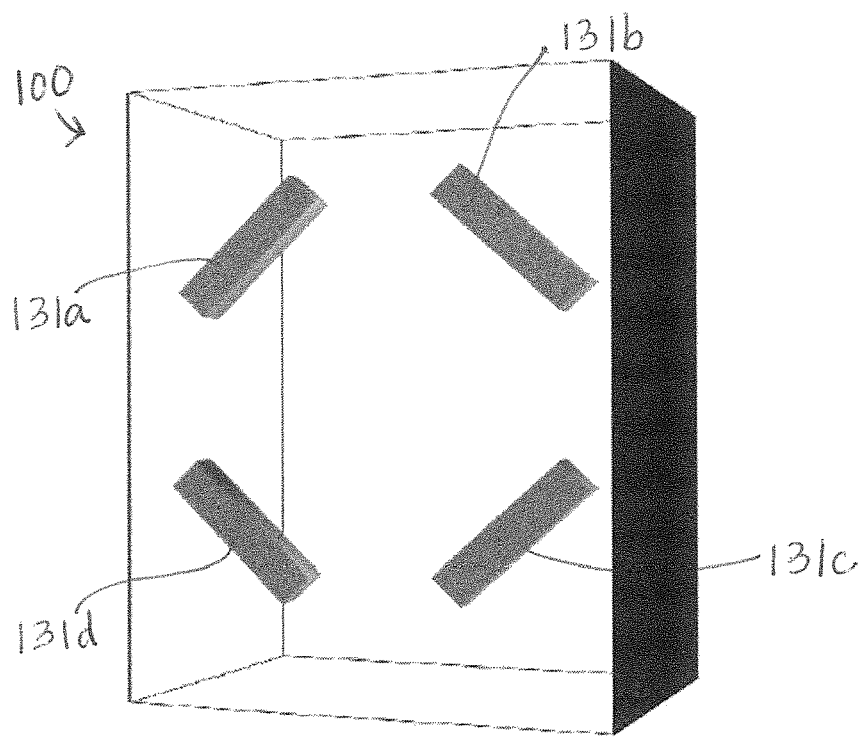
FIG. 13 is a top perspective view of four radiant-energy emitter fixtures according to an example embodiment, the emitter fixtures mounted to the ceiling in a space and in an inactive position.
Figure 14:
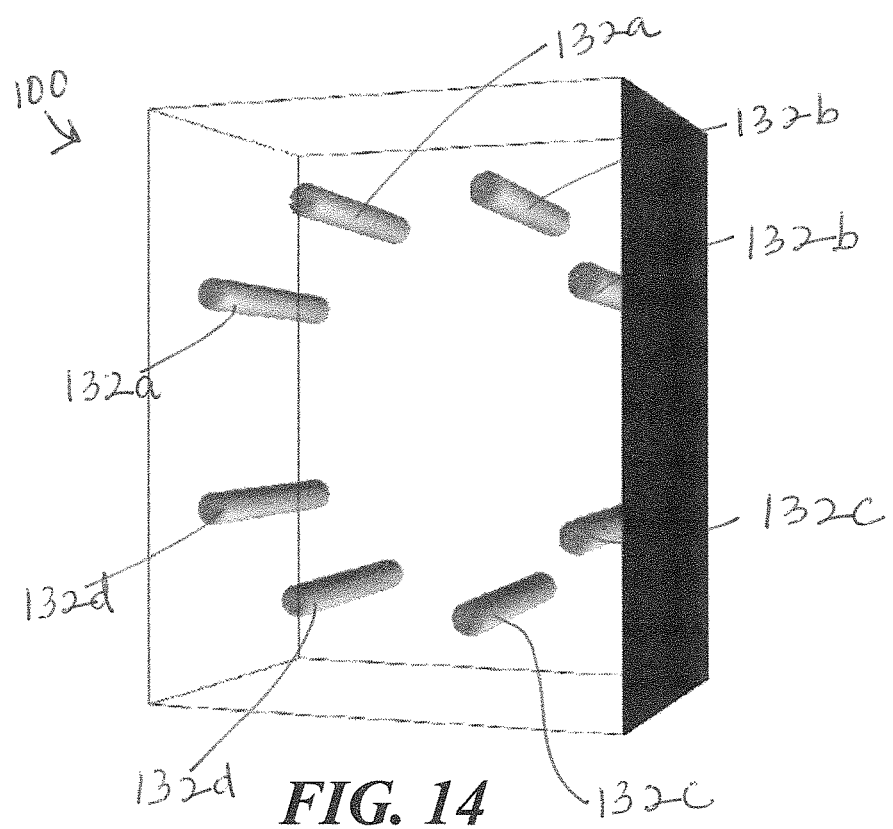
FIG. 14 is a top perspective view of radiant-energy emitters from the four emitter fixtures of FIG. 13 in an active position according to an example embodiment.
Figure 16:
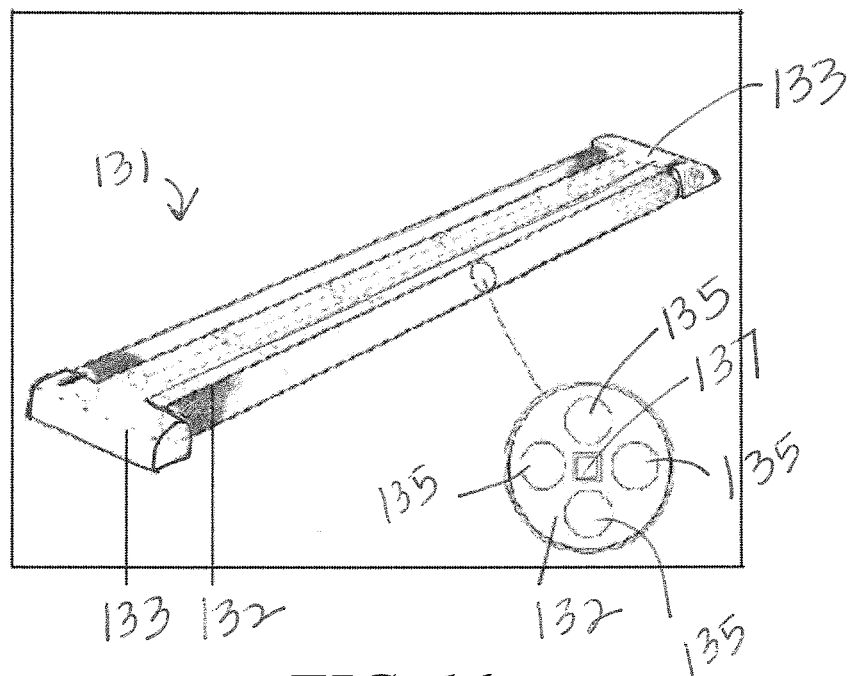
FIG. 16 is a perspective view of an emitter fixture having two radiant-energy emitters in an inactive position according to an example embodiment.
Figure 17:
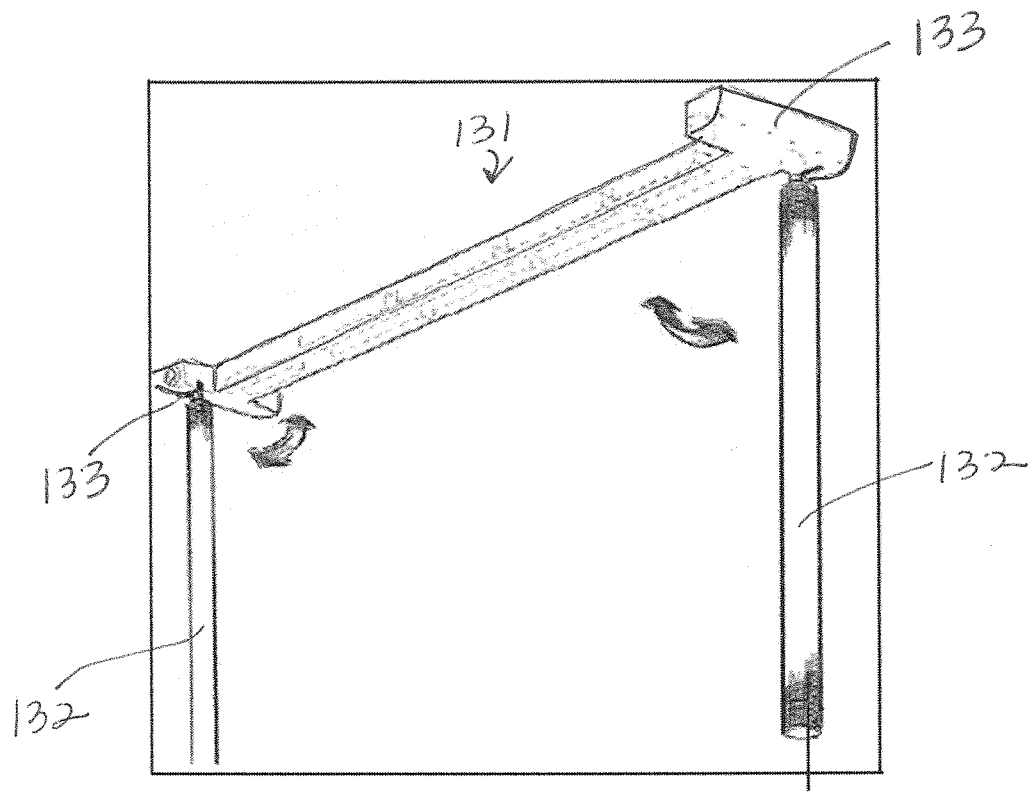
FIG. 17 is a perspective view of an emitter fixture having two radiant-energy emitters in an active position according to an example embodiment.
Figure 18:
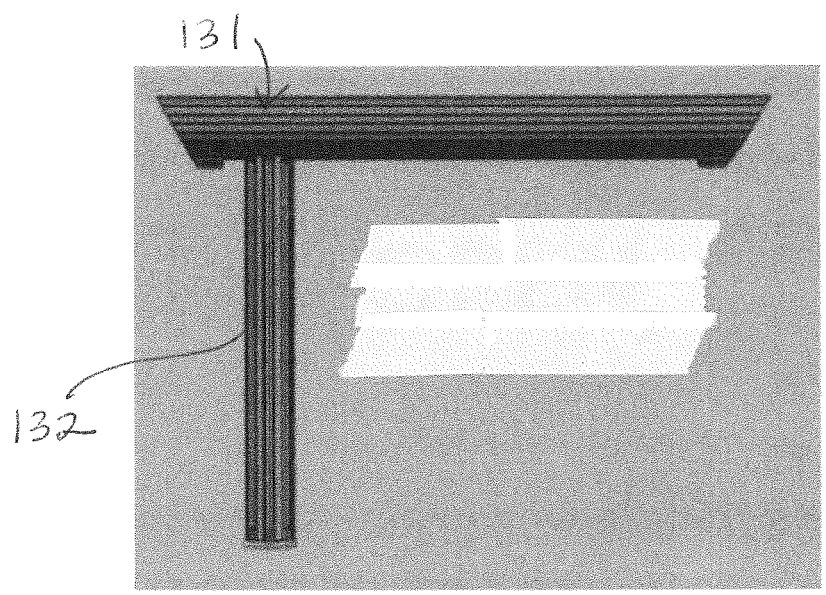
FIG. 18 is a side elevational view of an emitter fixture having one radiant-energy emitter in an active position according to an example embodiment.

In another example embodiment, the irradiation system 130 may disinfect a space by automatically repositioning radiant-energy emitters 132 from a disengaged, inactive position where emission of radiant energy is terminated (FIG. 13) into a deployed, active position for emission of radiant energy (FIG. 14) that is closer to target surfaces. A radiant-energy emitting fixture 131 housing one or more radiant-energy emitters 132 may be mounted to a wall or ceiling, or be free to move about the room 100 via a robotic drive system. FIG. 13 is a schematic representation of an example embodiment of four radiant-energy emitter fixtures 131a-d in an inactive position mounted to a ceiling, and FIG. 14 depicts eight radiant-energy emitters 132a-d, two from either emitter fixture 131a-d, in an active position extending into the room 100. FIGS. 16 and 17 illustrate a radiant-energy emitter fixture 131 with two radiant-energy emitters 132 in the inactive and active positions, respectively. As shown, each radiant-energy emitter fixture 131 includes an area 133 for housing electronics and a motor drive system for moving the radiant-energy emitters 132. In an example embodiment illustrated in the inset drawing of FIG. 16, each radiant-energy emitter 132 may include four UV-C lamps 135 surrounding a reflective coated polycarbonate tube 137, wherein the UV-C lamps 135 may be housed within a stainless steel rod or wire periphery for safety purposes. FIG. 18 depicts an example embodiment where the radiant-energy emitter fixture 131 houses one radiant-energy emitter 132.

Figure 15:
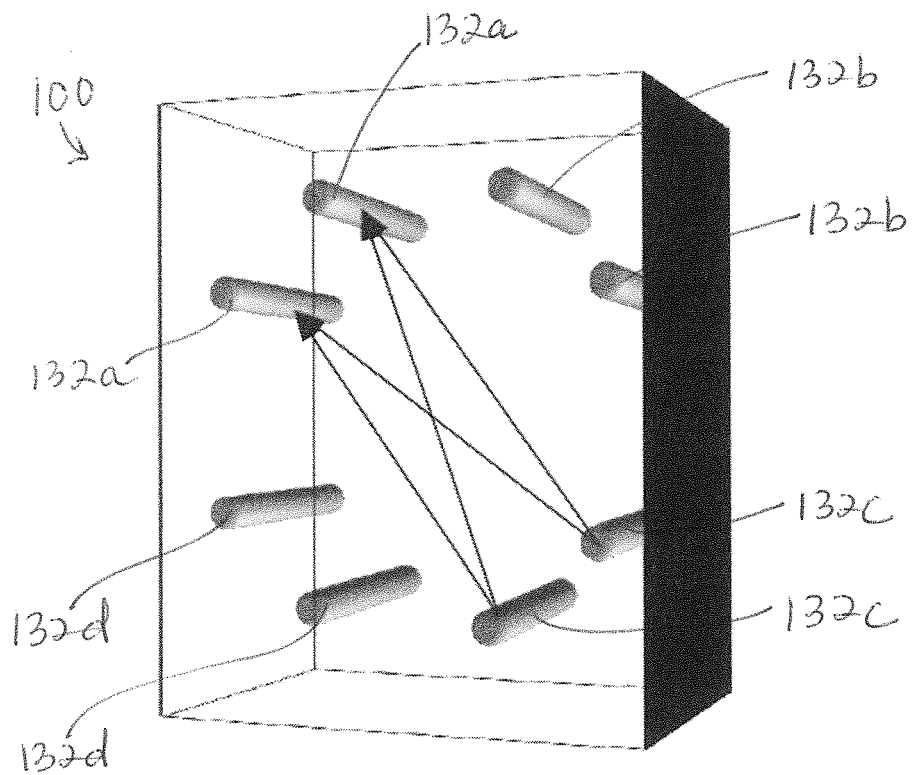
FIG. 15 is a top perspective view of radiant-energy emitters in an active position as in FIG. 14, wherein the arrows indicate reciprocal field sensing wherein each emitter fixture includes a radiant-energy sensor that detects the electromagnetic field from the opposing radiant-energy emitter.

The irradiation system 130 may monitor radiant energy dosing in real time by the reciprocal reading of radiant energy output from a positionally opposing radiant energy emitter fixtures 131, as illustrated by the arrows in FIG. 15. Reciprocal reading of electromagnetic emission is accomplished by radiant-energy sensors mounted on an emitter fixture aimed to detect the primary emission of radiant energy from an opposing emitter fixture. In this way, installation of emitter fixtures and sensors may be simplified and modular.

On initiation of a disinfection cycle, control logic may send a command to move radiant-energy emitters 132 from an inactive position into an active position. The radiant-energy emitters 132 are then activated to begin irradiation of exposed surfaces. Radiant-energy values are detected at the radiant-energy sensors, and control logic may send a command to reposition one or more radiant-energy emitters 132 or reflectors, or to return one or more radiant-energy emitters 132 to the inactive position based on sensor readings. Other orientations besides the inactive and active positions illustrated herein, such as partial deployment, and more complex movements may be used to achieve optimal positioning of the radiant-energy emitters 132. The irradiation system 130 can use an accelerometer based, IR reflection detection, IR beam detection, level sensing switch, or motor stall current to sense end of motion of the radiant-energy emitters 132. In one example embodiment, as a safety feature, any object that obstructs the path of the moving radiant-energy emitter 132 stops the radiant-energy emitter 132 without force from a motor drive system applied to the obstruction. In another example embodiment, an image analysis system may be utilized that has the ability to detect motion and changes in the target environment, which may be important to prevent emitter activation in the event of an obstruction or occupancy.

Several wavelengths of electromagnetic energy are known to be antimicrobial. In the irradiation system 130, radiant-energy emitters 132 may include a single antimicrobial wavelength or a combination of several wavelengths to produce an optimal radiant energy flux. Infrared energy creates penetrating heat that may be used as an antimicrobial, wherein this wavelength may be valuable for metal surfaces that require high level sterilization. UV-C band energy is a low penetration wavelength that is antimicrobial and is effective in treating air and hard surfaces. UV-A and UV-B band energy are also antimicrobial and penetrate further than UV-C, such that a combination of A, B, and C wavelengths may produce an optimized effect. High level sterilization may be achieved by the use of x-rays and gamma rays, wherein applications may exist in the food or sterile items industry for these highly penetrating wavelengths. Radio frequencies have been shown to have the capability to be bacteriostatic. Specific applications may exist for automated positioning and sensing radio frequency emission for the purpose of suspending bacterial replication. This technology may branch into the treatment of human disease in vivo, wherein a system may position a radiant-energy emitter proximal to an infection site and deliver a calibrated bacteriostatic dose to one or more sites.

Figure 19:
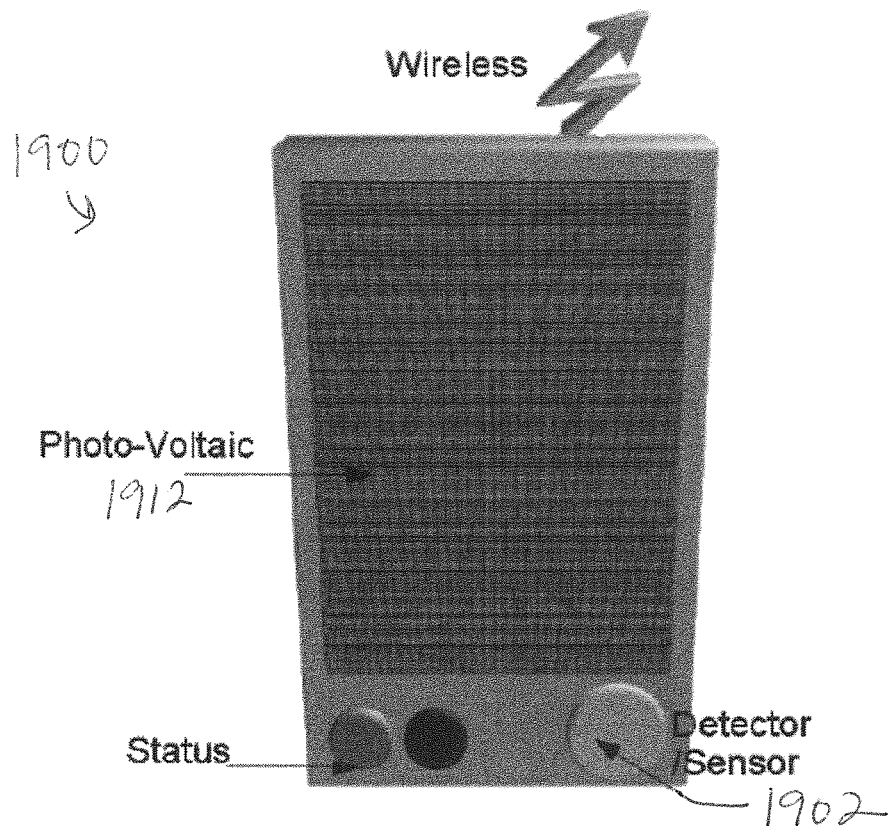
FIG. 19 is a front elevational view of a wireless radiant-energy sensor according to an example embodiment.
Figure 20:
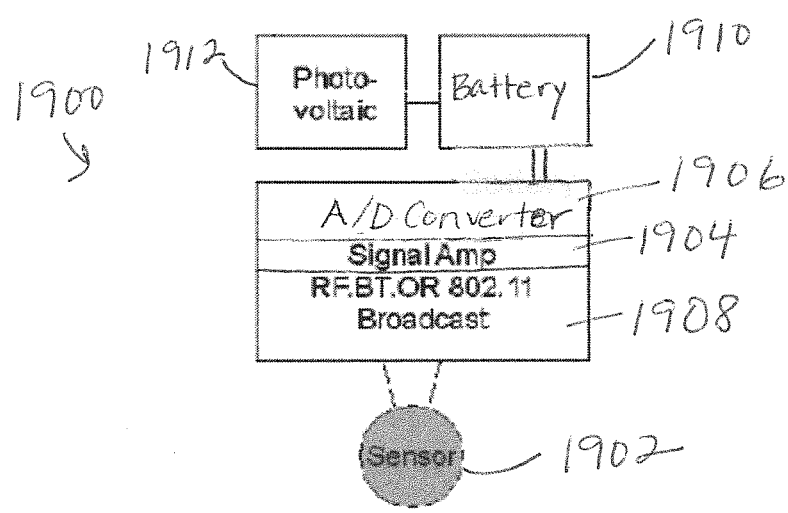
FIG. 20 is a block diagram showing components of the wireless radiant-energy sensor of FIG. 19 according to an example embodiment.

In some circumstances it may be desirable to monitor primary radiant energy field in a remote location. In an example embodiment, a wireless flux sensor system 1900 may be employed as shown in FIGS. 19 and 20 that includes a sensor 1902, amplifier 1904, A/D converter 1906, broadcast system (Bluetooth, 802.11, RF, or other) 1908, battery system 1910, and photo-voltaic cell 1912. The photo-voltaic cell 1912 converts flux into power to charge the battery 1910 and drive the wireless flux sensor system 1900.

When using radiant energy to disinfect a room, the size of the space, room temperature, and relative humidity effect the time to achieve a required dose. A way to read all three variables so that the information can be used for treatment timing provides a benefit in the absence of an ability to read direct radiant energy levels or in conjunction with radiant energy readings to determine an accurate treatment time. Information regarding one or more of room size (determined via ultrasound, laser, Doppler, or other methods), temperature, and relative humidity, may be forwarded to a control system via low voltage wiring or other wireless technologies, such as Bluetooth, 802.11, RF, or others. Room object density may also be used as a factor in dosing or any combination of the methods described herein.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

In the foregoing detailed description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the detailed description, with each claim standing on its own as defining separately claimed subject matter.

What is claimed is:

1. A system for irradiating an area with ultraviolet light, comprising:
   a mobile housing;
   a receiver associated with the housing;
   at least one power source;
   at least one radiant-energy emitter for continuously emitting ultraviolet light during operation of the system for disinfection of the area, the at least one radiant-energy emitter associated with the housing and powered by the at least one power source, wherein ultraviolet light emitted from the at least one radiant-energy emitter is capable of being varied based on power received from the power source;
   at least one radiant-energy sensor assembly, the sensor assembly including a first radiant-energy sensor, a second radiant-energy sensor, and a transmitter, the at least one radiant-energy sensor assembly detecting an amount of ultraviolet light from the first and second radiant-energy sensors during operation of the system and transmitting information regarding the amount to the receiver;
   wherein the amount of ultraviolet light detected by the first radiant-energy sensor includes both ultraviolet light created by the at least one radiant-energy emitter that is received directly from the at least one radiant-energy emitter and ultraviolet light created by the at least one radiant-energy emitter that is received after reflection off items in the area; and wherein the amount of ultraviolet light detected by the second radiant-energy sensor includes ultraviolet light created by the at least one radiant-energy emitter that is received after reflection off items in the area, but does not include ultraviolet light received directly from the at least one radiant-energy emitter; and control logic configured to terminate the emitting of ultraviolet light by the at least one radiant-energy emitter based on the information transmitted from the transmitter to the receiver, wherein the information includes data relating to disinfection of the area.

2. The system of claim 1, wherein the housing is movable via a robotic drive system.

3. The system of claim 1, wherein the ultraviolet light has wavelengths in a range from about 100 nanometers to about 280 nanometers (UV-C).

4. The system of claim 1, wherein the control logic is configured to position the at least one radiant-energy emitter between an inactive position and an active position based upon the amount of ultraviolet light detected at the first and second radiant-energy sensors.

5. The system of claim 1, wherein the at least one radiant-energy emitter includes an adjustable reflector to reflect emitted ultraviolet light in a particular direction.

6. The system of claim 1, further comprising a hygrometer in communication with the control logic for determining an amount of relative humidity in the area.

7. The system of claim 1, further comprising an image analysis system in communication with the control logic for detecting motion and changes in the area to prevent emitter activation in the event of an obstruction or occupancy.

8. The system of claim 1 wherein the at least one radiant-energy sensor assembly is remote from the housing.

9. A system for irradiating an area with ultraviolet light, comprising:
at least one power source;
a housing having at least one radiant-energy emitter for continuously emitting ultraviolet light during operation of the system for disinfection of the area, the at least one radiant-energy emitter associated with the housing and powered by the at least one power source, wherein the at least one radiant-energy emitter emits an adjustable flux of ultraviolet light during operation of the system dependent on the power received from the at least one power source;
at least one wireless sensor assembly, the wireless sensor assembly including a first radiant-energy sensor, a second radiant energy sensor, and a transmitter, the at least one wireless sensor assembly detecting an amount of ultraviolet light during operation of the system and transmitting information regarding the amount to a receiver that is capable of communicating with the at least one radiant-energy emitter;
wherein the amount of ultraviolet light detected by the first radiant-energy sensor includes both ultraviolet light created by the at least one radiant-energy emitter that is received directly from the at least one radiant-energy emitter and ultraviolet light created by the at least one radiant-energy emitter that is received after reflection off items in the area; and
wherein the amount of ultraviolet light detected by the second radiant-energy sensor includes ultraviolet light created by the at least one radiant-energy emitter that is received after reflection off items in the area, but does not include ultraviolet light received directly from the at least one radiant-energy emitter; and
control logic configured to vary the power received by the at least one radiant-energy emitter and configured to terminate the emitting of ultraviolet light by the at least one radiant-energy emitter based on the information transmitted from the transmitter to the receiver, wherein the information includes data relating to disinfection of the area.

10. The system of claim 9, wherein the wireless sensor assembly includes a battery system for powering the assembly.

11. The system of claim 10, wherein the wireless sensor assembly includes a photo-voltaic cell for converting flux into power to charge the battery system.

12. The system of claim 9, wherein the housing is mobile.

13. The system of claim 9, wherein the ultraviolet light has wavelengths in a range from about 100 nanometers to about 280 nanometers (UV-C).

14. The system of claim 9 wherein the at least one wireless sensor assembly is remote from the housing.

15. A device for disinfecting an area, comprising:
a base assembly including a housing;
at least one power source;
at least one radiant-energy emitter mounted to the housing for continuously emitting ultraviolet light during operation of the device for disinfection of the area, the at least one radiant-energy emitter powered by the at least one power source;
a reflector mounted to the housing and movable with respect to the housing, the reflector operable to direct the ultraviolet light from the at least one radiant-energy emitter onto the area to be disinfected;
a plurality of radiant-energy sensors adapted to detect the ultraviolet light emitted from the at least one radiant-energy emitter; an actuator associated with the reflector which when driven causes the reflector to change position with respect to the housing to allow the reflector to direct the ultraviolet light from the emitter within the area to be disinfected; and
control logic adapted to control the actuator and the at least one power source such that an amount of radiant energy detected at each of the plurality of radiant-energy sensors approaches equality.

16. The device of claim 15, further comprising a computer system in communication with the at least one emitter and the actuator, the computer system including a remote control device separate from the housing.

17. The device of claim 16, wherein the computer system is adapted to detect motion or changes in the area to prevent emitter activation in the event of an obstruction or occupancy.

18. The device of claim 15, further comprising a laser for estimating a size of the area.

19. A device for disinfecting an area, comprising:
a mobile base assembly including a housing;
at least one power source;
at least one radiant-energy emitter mounted to the housing for continuously emitting ultraviolet light during operation of the device for disinfection of the area, the at least one radiant-energy emitter powered by the at least one power source;
a reflector mounted to the housing and movable with respect to the housing, the reflector operable to direct the ultraviolet light from the at least one radiant-energy emitter onto the area to be disinfected;

a plurality of radiant-energy sensors adapted to detect the ultraviolet light emitted from the at least one radiant-energy emitter;
a drive mechanism including at least one gear operably connected to the reflector which causes the reflector to rotate about an axis and change position with respect to the housing; and
control logic adapted to control the drive mechanism and the at least one power source such that an amount of radiant energy detected at each of the plurality of radiant-energy sensors approaches equality.

20. The device of claim 19, wherein the at least one emitter is powered to emit Ultraviolet-C radiation for the disinfection of surfaces within the area.

21. A device for disinfecting an area, comprising:
a base assembly including a housing;
at least one power source;
at least one radiant-energy emitter attached to the housing for continuously emitting ultraviolet light during operation of the device for disinfection of the area, the at least one radiant-energy emitter powered by the at least one power source;
a plurality of radiant-energy sensors adapted to detect the ultraviolet light emitted from the at least one radiant-energy emitter;
a reflector mounted to the housing and movable with respect to the housing, the reflector configured to direct the ultraviolet light from the at least one radiant-energy emitter onto the area to be disinfected;
a motor configured to rotate the reflector relative to the housing; and
control logic adapted to control the motor and the at least one power source such that an amount of radiant energy detected at each of the plurality of radiant-energy sensors approaches equality.

22. A device comprising:
a moveable base assembly;
a power component for supplying electrical power coupled to the base assembly;
a plurality of adjustable radiant-energy emitters which receive power from the power component, the plurality of emitters mounted to the base assembly in a generally vertical orientation and configured to emit ultraviolet light into an area, the ultraviolet (UV) light having wavelengths in a range from about 100 nanometers to about 280 nanometers (UV-C), wherein an amount of ultraviolet light emitted from the plurality of adjustable radiant-energy emitters varies;
a first radiant-energy sensor mounted to the base assembly and detecting an amount of ultraviolet light, wherein the amount of ultraviolet light detected by the first radiant-energy sensor includes both ultraviolet light created by the plurality of radiant-energy emitters that is received directly from a first one of the plurality of radiant-energy emitters and ultraviolet light created by a second one of the plurality of radiant-energy emitters that is received after reflection off of a structure in the area;
a second radiant-energy sensor mounted to the base assembly and detecting an amount of ultraviolet light, wherein the amount of ultraviolet light detected by the second radiant-energy sensor includes ultraviolet light created by the plurality of radiant-energy emitters that is received directly from the second one of the plurality of radiant-energy emitters and ultraviolet light created by the first one of the plurality of radiant-energy emitters that is received after reflection off of a structure in the area; and
control logic in communication with the plurality of adjustable radiant-energy emitters and the first and second radiant-energy sensors, wherein the control logic terminates the emitting of ultraviolet light from the plurality of radiant-energy emitters when a total amount of ultraviolet light received by the first and second radiant-energy sensors exceeds a predetermined threshold value, wherein the threshold value is sufficient to allow the ultraviolet light to sanitize the area in which the plurality of radiant-energy emitters are located.

23. The device of claim 22, wherein the ultraviolet light detected at the first and second radiant-energy sensors includes ultraviolet light energy from at least two adjustable radiant-energy emitters of the plurality of adjustable radiant-energy emitters.

24. The device of claim 22, further comprising a network adaptor for transmitting location information to a system configured to store the location information and configured to generate reports at least partially based on the location information, wherein the location information identifies a particular location to be irradiated with a total amount of ultraviolet light emitted from the plurality of adjustable radiant-energy emitters, and receiving the threshold value from the system, wherein the threshold value is at least partially based on the information identifying the particular location.

25. The device of claim 24, wherein the network adaptor is operable to transmit collected information related to the emitting, the detecting, or the adjusting to a system configured to store the collected information and configured to generate reports at least partially based on the collected information.

* * * * *